United States Patent
Bundock et al.

(10) Patent No.: US 11,371,051 B2
(45) Date of Patent: Jun. 28, 2022

(54) METHOD FOR TARGETED DNA ALTERATION IN PLANT CELLS

(71) Applicant: Keygene N.V., Wageningen (NL)

(72) Inventors: Paul Bundock, Wageningen (NL); Anita Ketelaars-Bonné, Wageningen (NL)

(73) Assignee: KEYGENE N.V., Wageningen (NL)

( * ) Notice: Subject to any disclaimer, the term of this patent is extended or adjusted under 35 U.S.C. 154(b) by 0 days.

(21) Appl. No.: 16/310,764

(22) PCT Filed: Jun. 20, 2017

(86) PCT No.: PCT/NL2017/050408
§ 371 (c)(1),
(2) Date: Dec. 17, 2018

(87) PCT Pub. No.: WO2017/222370
PCT Pub. Date: Dec. 28, 2017

(65) Prior Publication Data
US 2019/0367933 A1    Dec. 5, 2019

(30) Foreign Application Priority Data
Jun. 20, 2016   (NL) .................................. 2016998

(51) Int. Cl.
*C12N 15/82* (2006.01)
*C12N 9/22* (2006.01)
*C12N 15/11* (2006.01)

(52) U.S. Cl.
CPC .......... *C12N 15/8213* (2013.01); *C12N 9/22* (2013.01); *C12N 15/11* (2013.01); *C12N 2310/20* (2017.05); *C12N 2800/80* (2013.01)

(58) Field of Classification Search
CPC combination set(s) only.
See application file for complete search history.

(56) References Cited

U.S. PATENT DOCUMENTS

2014/0090116 A1*   3/2014   Ainley .................... C12N 9/22
                                              800/312

FOREIGN PATENT DOCUMENTS

| WO | WO 2009/082190 A1 | 7/2009 |
| WO | WO-2014/065596 A1 | 5/2014 |
| WO | WO 2014/194190 A1 | 12/2014 |

OTHER PUBLICATIONS

Heler et al. 2015 Nature 519:199-202 (Year: 2015).*
Hsu et al (2013 Nature Biotechnology 31:827-832) (Year: 2013).*
Lyzniketal (1989 Plant Cell Reports 8:292-295 (Year: 1989).*
Woo et al 2015 Nature Biotechnology 33:1162-1164 (Year: 2015).*
Li et al., "Multiplex and homologous recombination-mediated genome editing in *Arabidopsis* and *Nicotiana benthamiana* using guide RNA and Cas9", Nature Biotechnology, vol. 31, No. 8, Jun. 23, 2013, No. 8, pp. 688-691.
Li et al., "Multiplex and homologous recombination-mediated plant genome editing via guide RNA/Cas9", Nature Biotechnology, Aug. 8, 2013, pp. 1-15.
Yoo et al., "*Arabidopsis* mesophyll protoplasts: a versatile cell system for transient gene expression analysis", Nature Protocols, Nature Publishing Group, vol. 2, No. 7, Jan. 1, 2007, pp. 1750-2799.
Shaefflet et al., "Single Cell Nurse Culture of Tobacco Protoplasts: Physiological Analysis of Conditioning Factors", Journal of Plant Physiology, vol. 137, No. 1, 1990, pp. 95-101.
Tan et al., "Regeneration of leaf mesophyll protoplasts of tomato cultivars (*L. esculentum*): factors important for efficient protoplast culture and plant regeneration", Plant Cell Reports, vol. 6, No. 3, Jun. 1, 1987, pp. 172-175.
Bortesi et al., "The CRISPR/Cas9 system for plant genome editing and beyond", Biotechnology Advances, vol. 33, No. 1, Jan. 1, 2015, pp. 41-52.
International Search Report issued in PCT/NL2017/050408 dated Sep. 19, 2017.
Jinek et al.: "A Programmable Dual-RNA-Guided DNA Endonuclease in Adaptive Bacterial Immunity", Aug. 17, 2012, Science, vol. 337, pp. 816-821.
Woo et al., "DNA-free genome editing in plants with preassembled CRISPR-Cas9 ribonucleoproteins", Nat Biotechnol, vol. 3, No. 11,2015: pp. 1162-1164 (4 pages).

* cited by examiner

*Primary Examiner* — Brent T Page
(74) *Attorney, Agent, or Firm* — Sunit Talapatra; Foley & Lardner LLP

(57) ABSTRACT

Disclosed is a new method of providing plant cells with a targeted alteration in a DNA molecule. The method comprises contacting a population of plant cells comprising a DNA molecule, the DNA molecule having a target sequence, with an aqueous medium, wherein the aqueous medium comprises a CRISPR associated protein (CAS protein) or a CAS-like protein, and a CRISPR-Cas system guide RNA that hybridizes with the target sequence, and wherein the aqueous medium comprises polyethylene glycol (PEG), but needs to be substantially free of glycerol.

Figure 4:
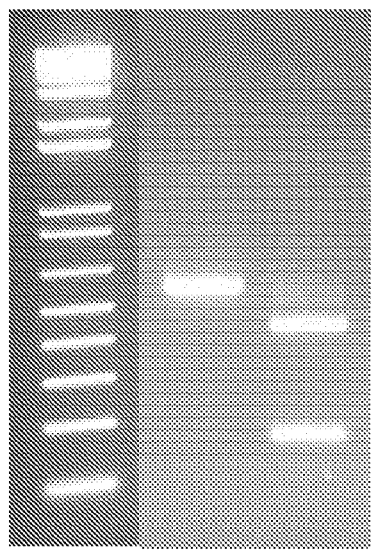

20 Claims, 8 Drawing Sheets
Specification includes a Sequence Listing.

Fig. 1

MGWTLNSAGYLLGKINLKALAALAKKILAMGSSHHHHHHVYPYDVPDYAELPP*KKKRK*VGI
ENLYFQGDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFHRLEESFLVEEDKKHERHPIFGN
IVDEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEIT
KAPLSASMIKRYDEHHQDLTLLKALVRQQLPEKYKEIFFDQSKNGYAGYIDGGASQEEFYKFI
KPILEKMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLKED
YFKKIECFDSVEISGVEDRFNASLGTYHDLLKIIKDKDFLDNEENEDILEDIVLTLTLFEDREMIE
ERLKTYAHLFDDKVMKQLKRRRYTGWGRLSRKLINGIRDKQSGKTILDFLKSDGFANRNFMQ
LIHDDSLTFKEDIQKAQVSGQGDSLHEHIANLAGSPAIKKGILQTVKVVDELVKVMGRHKPEN
IVIEMARENQTTQKGQKNSRERMKRIEEGIKELGSQILKEHPVENTQLQNEKLYLYYLQNGRD
MYVDQELDINRLSDYDVDHIVPQSFLKDDSIDNKVLTRSDKNRGKSDNVPSEEVVKKMKNY
WRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEF
VYGDYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKKYGGF
DSPTVAYSVLVVAKVEKGKSKKLKSVKELLGITIMERSSFEKNPIDFLEAKGYKEVKKDLIIKL
PKYSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGAPAAFK
YFDTTIDRKRYTSTKEVLDATLIHQSITGLYETRIDLSQLGGD

Fig. 2

ATGGGAAGAGGATCGCATCACCACCATCATCATAAGCTTCCAAAGAAGAAGAGGAAGGT
TCTCGAGATGGATAAGAAGTACTCTATCGGACTTGATATCGGAACTAACTCTGTGGGATG
GGCTGTGATCACTGATGAGTACAAGGTGCCATCTAAGAAGTTCAAGGTTTTGGGAAACAC
TGATAGGCACTCTATCAAGAAAAACCTTATCGGAGCTTTGCTTTTCGATTCTGGTGAGACT
GCTGAGGCTACTAGGCTTAAGAGGACTGCTAGAAGAAGGTACACTAGAAGAAAGAACAG
GATCTGCTACCTTCAAGAGATCTTCTCTAACGAGATGGCTAAAGTGGATGATTCATTCTTC
CACAGGCTTGAAGAGTCTTTCTTGGTGGAAGAAGATAAGAAGCACGAGAGGCACCCAATC
TTCGGAAACATCGTTGATGAGGTGGCATACCACGAGAAGTACCCAACTATCTACCACCTT
AGGAAGAAGCTTGTTGATTCTACTGATAAGGCTGATCTTAGGCTTATCTACCTTGCTCTTG
CTCACATGATCAAGTTCAGGGGACACTTCCTTATCGAGGGTGATCTTAACCCAGATAACTC
TGATGTGGATAAGCTTTTCATCCAGCTTGTGCAGACTTACAACCAGCTTTTCGAAGAGAAC
CCAATCAACGCTTCTGGTGTGGATGCTAAGGCTATCCTTTCTGCTAGGCTTTCTAAGTCTA
GAAGGCTTGAGAACCTTATTGCTCAGCTTCCAGGTGAGAAGAAGAACGGACTTTTCGGAA
ACTTGATCGCTCTTTCTCTTGGACTTACTCCAAACTTCAAGTCTAACTTCGATCTTGCTGAG
GATGCAAAGCTTCAGTTGTCTAAGGATACTTACGATGATGATCTTGATAACTTGCTTGCTC
AGATCGGAGATCAGTACGCTGATCTTTTCCTTGCTGCTAAAAACCTTTCTGATGCTATCTT
GCTTTCTGATATCCTTAGGGTGAACACTGAGATCACTAAGGCTCCACTTTCTGCTTCTATG
ATCAAGAGGTACGATGAGCACCACCAGGATCTTACTTTGCTTAAGGCTCTTGTGAGGCAG
CAGTTGCCAGAGAAGTACAAAGAGATTTTCTTCGATCAGTCTAAGAACGGATACGCTGGT
TACATCGATGGTGGTGCATCTCAAGAAGAGTTCTACAAGTTCATCAAGCCAATCCTTGAG
AAGATGGATGGAACTGAAGAGTTGCTTGTGAAGCTTAACAGAGAGGATCTTCTTAGGAAG
CAGAGGACTTTCGATAACGGATCTATCCCTCACCAGATCCACCTTGGAGAGCTTCACGCTA
TCTTGAGAAGGCAAGAGGATTTCTACCCATTCTTGAAGGATAACAGGGAAAAAATCGAGA
AGATTCTTACTTTCAGGATCCCTTACTACGTGGGACCACTTGCTAGGGGAAATTCTAGGTT
CGCTTGGATGACTAGGAAGTCTGAAGAGACTATCACTCCATGGAACTTCGAAGAGGTGGT
GGATAAGGGTGCTAGTGCTCAGTCTTTCATCGAGAGGATGACAAACTTCGATAAGAACCT
TCCAAACGAGAAGGTGTTGCCAAAGCACTCTTTGCTTTACGAGTACTTCACTGTGTACAAC
GAGCTTACTAAGGTGAAGTACGTGACAGAGGGAATGAGGAAGCCAGCTTTCTTGTCTGGT
GAGCAAAAGAAGGCTATCGTTGATCTTTTGTTCAAGACTAATAGAAAGGTGACAGTGAAG
CAGCTTAAAGAGGATTACTTCAAAAAGATCGAGTGCTTCGATTCAGTTGAGATCTCTGGT
GTTGAGGATAGGTTCAACGCATCTTTGGGAACTTACCACGATTTGTTGAAGATTATCAAGG
ATAAGGATTTCTTGGATAACGAGGAAAACGAGGATATCTTGGAGGATATCGTGCTTACTC
TTACTCTTTTCGAGGATAGAGAGATGATTGAAGAAAGGCTTAAAACTTACGCTCACCTTTT
CGATGATAAGGTGATGAAGCAGTTGAAGAGAAGAAGATACACAGGTTGGGGAAGGTTGT

Fig. 2 cont.

CTAGGAAGCTTATCAACGGAATCAGGGATAAGCAGTCTGGTAAGACTATCTTGGATTTCC
TTAAGTCTGATGGATTCGCTAATAGGAACTTCATGCAGTTGATCCACGATGATTCTTTGAC
TTTCAAAGAGGATATCCAGAAGGCTCAGGTTTCAGGACAGGGTGATAGTTTACACGAGCA
CATTGCTAACCTTGCTGGATCTCCTGCAATCAAGAAGGGAATCTTGCAGACTGTGAAGGTT
GTGGATGAGTTGGTGAAGGTGATGGGAAGGCATAAGCCAGAGAACATCGTGATCGAAAT
GGCTAGAGAGAACCAGACTACTCAGAAGGGACAGAAGAACTCTAGGGAAAGGATGAAGA
GGATCGAAGAGGGAATCAAAGAGCTTGGATCTCAGATCCTTAAAGAGCACCCAGTTGAG
AACACTCAGCTTCAGAACGAGAAGCTTTACCTTTACTACTTGCAGAACGGAAGGGATATG
TATGTGGATCAAGAGTTGGATATCAACAGGTTGTCTGATTATGATGTTGATCACATCGTGC
CACAGTCTTTTTTGAAGGATGATTCTATCGATAACAAGGTGTTGACTAGGTCTGATAAGAA
CAGGGGAAAGTCTGATAACGTTCCATCTGAAGAGGTTGTGAAAAAGATGAAGAACTATTG
GAGGCAGCTTCTTAACGCTAAGTTGATCACTCAGAGGAAGTTCGATAATTTGACTAAGGC
TGAGAGGGGAGGATTGTCTGAGCTTGATAAGGCAGGATTCATCAAGAGGCAGTTGGTTGA
GACTAGGCAGATCACAAAGCACGTGGCACAGATCCTTGATTCTAGGATGAACACTAAGTA
TGATGAGAACGATAAGTTAATCAGGGAAGTTAAGGTGATCACTTTGAAGTCTAAGCTTGT
GTCTGATTTTAGGAAGGATTTCCAATTCTACAAGGTGAGAGAGATCAACAACTACCACCA
CGCTCACGATGCTTACCTTAACGCTGTTGTGGGAACTGCTTTGATCAAGAAGTATCCAAAG
TTGGAGTCTGAGTTCGTGTACGGTGATTACAAGGTGTACGATGTGAGGAAGATGATCGCT
AAGTCAGAGCAAGAGATCGGAAAGGCTACTGCTAAGTATTTCTTCTACTCTAACATCATG
AATTTCTTCAAGACAGAGATCACTCTTGCTAACGGTGAGATTAGGAAGAGGCCACTTATC
GAGACAAATGGTGAGACAGGTGAGATCGTGTGGGATAAGGGAAGGGATTTCGCTACTGT
GAGAAAGGTGTTGTCTATGCCACAGGTGAACATTGTGAAGAAAACTGAGGTGCAGACTGG
TGGATTCTCTAAAGAGTCTATCCTTCCAAAGAGGAACTCTGATAAGTTGATTGCTAGGAA
AAAGGATTGGGATCCAAAAAAGTACGGTGGATTCGATTCTCCAACTGTGGCTTACTCTGT
GCTTGTGGTGGCTAAGGTTGAGAAGGGAAAATCAAAGAAATTGAAGTCTGTGAAAGAGC
TTCTTGGAATCACTATCATGGAAGGTCATCTTTCGAGAAGAACCCTATCGATTTCCTTGA
GGCTAAGGGATACAAAGAGGTGAAGAAGGATCTTATCATCAAGCTTCCAAAGTACTCACT
TTTCGAGCTTGAGAATGGAAGAAAGAGGATGCTTGCTTCTGCTGGTGAGTTGCAGAAGGG
TAACGAACTTGCTTTGCCTTCTAAGTACGTTAACTTCCTTTACCTTGCTTCTCACTACGAGA
AGTTGAAGGGATCTCCAGAGGATAACGAACAAAAGCAGTTGTTCGTTGAGCAGCACAAG
CACTACCTTGATGAGATCATCGAGCAGATCTCTGAGTTCTCTAAGAGGGTTATCTTGGCTG
ATGCAAACCTTGATAAGGTGTTGAGTGCTTACAACAAACATAGGGATAAGCCAATCAGAG
AGCAGGCTGAGAACATCATCCACCTTTTCACTTTGACTAACCTTGGTGCTCCAGCTGCTTT
CAAGTACTTCGATACAACTATTGATAGAAAGAGGTACACTTCTACAAAAGAGGTTTTGGA
TGCTACTTTGATCCACCAGAGTATCACTGGACTTTACGAGACTAGGATCGATTTGTCTCAG
CTTGGTGGTGATTGA

Fig. 3

<u>GGAGTGATCAAAAGTCCCACATCGATCAGGTGATATATAGCAGCTTAGTTTATATAATGA
TAGAGTCGACATAGCGATTG</u>ttactgcattccatactcga*GTTTTAGAGCTAGAAATAGCAAGTTAAAATA
AGGCTAGTCCGTTATCAACTTGAAAAAGTGGCACCGAGTCGGTGCTTTTTTT*CTAGACCCAGCT
TTCTTGTACAAAGTTGGCATTACGCT

Fig. 5

| | | |
|---|---|---|
| WT | TTACTGCATTCCATACTCGA | |
| | TTACTGCATTCCATAC--GA | -2 |
| | TTACTGCAT-------CGA | -8 |
| | TTACTGCATTCC-------A | -7 |
| | TTACTGCATTCCATAC-CGA | -1 |
| | TTACTGCATTCCAT---CGA | -3 |

Fig. 6

```
WT       TTACTGCATTCCATACTCGA
1E11     TTACTGCATT------TCGA      -6
2C10A    TTACTGCAT--------CGA      -8
2C10B    TTACTGCATTCC-----CGA      -5
2D11     TTACTGCATTCCATACTTCG      +1
2H08     TTACTGCATTCCATACTTCG      +1
3A02     TTACTGCATTCCAT---CGA      -3
3A11     TTACTGCAT-------TCGA      -7 BI
3C01     TTACTGCATTCCATAC-CGA      -1
3C11     TTACTGCATTCCATAC-CGA      -1
3E06     TTACTGCATTC-------GA      -7
3G08     TTAC--------------GA      -14
4C05     TTACTGCATTCCATA-TCGA      -1
4C06     TTACTGCATTC-------GA      -7
4G08     TTACTGCATTCCATACTTCG      +1
5A07     TTACTGCATTCC-----CGA      -5
5B04     TTACTGCATTCCATACTTCG      +1
5B05     TTACTGCATTCC-----CGA      -5
5C09     TTACTGCATTCCATACTTCG      +1
5G10     TTACTG----------TCGA      -10 BI
6D02     TTACTGCATTCCATACTTCG      +1
6G07     TTACTGCAT--------CGA      -8 BI
7C08     TTACTGCATTCCATAC-CGA      -1
7G04     TTACTGCATTCCATACTTCG      +1 BI
8E10     TTACTGCATT------TCGA      -6
```

METHOD FOR TARGETED DNA ALTERATION IN PLANT CELLS

CROSS-REFERENCE TO RELATED APPLICATIONS

This application is the National Phase of International Patent Application No. PCT/NL2017/050408, filed Jun. 20, 2017, published on Dec. 28, 2017 as WO 2017/222370 A1, which claims priority to NL Patent Application No. 2016998, filed Jun. 20, 2016. The contents of these applications are herein incorporated by reference in their entirety.

STATEMENT REGARDING SEQUENCE LISTING

The sequence listing associated with this application is provided in text format in lieu of a paper copy, and it is hereby incorporated by reference into the specification. The name of the text file containing the sequence listing is 085342-2800_Sequence_Listing.txt. The text file is ~28 kb, was created on Jul. 6, 2020, and is being submitted electronically via EFS-Web.

BACKGROUND OF THE INVENTION

The process of deliberately creating changes in the genetic material of living cells generally has the goal of modifying one or more genetically encoded biological properties of that cell, or of the organism of which the cell forms part or into which it can regenerate. These changes can take the form of deletion of parts of the genetic material, addition of exogenous genetic material, or changes in the existing nucleotide sequence of the genetic material.

Methods of altering the genetic material of eukaryotic organisms have been known for over 20 years, and have found widespread application in plant, human and animal cells and micro-organisms for improvements in the fields of agriculture, human health, food quality and environmental protection.

The most common methods consist of adding exogenous DNA fragments to the genome of a cell, which will then confer a new property to that cell or its organism over and above the properties encoded by already existing genes (including applications in which the expression of existing genes will thereby be suppressed). Although many such examples are effective in obtaining the desired properties, these methods are nevertheless not very precise, because there is no control over the genomic positions in which the exogenous DNA fragments are inserted (and hence over the ultimate levels of expression), and because the desired effect will have to manifest itself over the natural properties encoded by the original and well-balanced genome.

On the contrary, methods of genome editing that will result in the addition, deletion or conversion of nucleotides in predefined genomic loci will allow the precise modification of existing genes.

Recently a novel method for targeted genome editing has been reported. CRISPRs (Clustered Regularly Interspaced Short Palindromic Repeats) are loci containing multiple short direct repeats and are found in 40% of the sequenced bacteria and 90% of sequenced archaea.

The CRISPR repeats form a system of acquired bacterial immunity against genetic pathogens such as bacteriophages and plasmids. When a bacterium is challenged with a pathogen, a small piece of the pathogen genome is processed by CRISPR associated proteins (Cas) and incorporated into the bacterial genome between CRISPR repeats. The CRISPR loci are then transcribed and processed to form so called crRNA's which include approximately 30 bps of sequence identical to the pathogen genome. These RNA molecules form the basis for the recognition of the pathogen upon a subsequent infection and lead to silencing of the pathogen genetic elements through either a RNAi like process or direct digestion of the pathogen genome.

The Cas9 protein (or protein with similar function) is an important component of the typeII CRISPR/Cas system and forms an endonuclease, when combined with the crRNA and a second RNA termed the trans-activating cRNA (tracrRNA), which targets the invading pathogen DNA for degradation by the introduction of DNA double strand breaks (DSBs) at the position in the genome defined by the crRNA.

Recently, Jinek et al. (2012, *Science* 337: 816-820) demonstrated that a single chain chimeric RNA produced by fusing an essential portion of the crRNA and tracrRNA was able to form a functional endonuclease in combination with Cas9. The CRISPR system can be used for genome editing in a wide range of different cell types.

The CRISPR system comprises basically two components: a "guide" RNA (gRNA) and a non-specific CRISPR-associated endonuclease (e.g. Cas9). The gRNA is a short synthetic RNA composed of a scaffold sequence necessary for Cas9-binding and a user-defined nucleotide "targeting" sequence which defines the genomic target to be modified. Thus, one can change the genomic target of the endonuclease (e.g. Cas9) by simply changing the targeting sequence present in the gRNA. CRISPR was originally employed to knock-out target genes in various cell types and organisms, but modifications to the enzymes have extended the application of CRISPR to selectively activate or repress target genes, purify specific regions of DNA, and even image DNA in live cells using fluorescence microscopy. Furthermore, the ease of generating gRNAs makes CRISPR one of the most scalable genome editing technologies and has been recently utilized for genome-wide screens.

Thus, a chimeric RNA can be designed to target a specific sequence in the eukaryotic genome, and DSBs can be induced at this sequence upon expression of e.g. the Cas9 protein and the chimeric RNA in the cell. Once a DNA DSB has been produced the cellular DNA repair machinery, particularly proteins belonging to the non-homologous end joining pathway, are involved in the re-ligation of the DNA ends. This process can lead to the loss or gain of a few nucleotides at the break, creating an INDEL mutation in the genomic DNA. When the DSB is induced in a coding sequence, any INDEL at this position may lead to an alteration in the protein reading frame and may function as a null mutation. Alternatively, any INDELs which lead to the deletion or insertion of multiples of three nucleotides (e.g. +3, +9, −6) will create in frame mutations which may influence protein function rather than eliminating it.

While DSB repair may be imperfect and may result in disruption of the open reading frame of the gene, Homology Directed Repair (HDR) may be used to generate specific nucleotide changes in the target DNA. In order to utilize HDR for gene alteration, a DNA "repair template" containing the desired sequence must be delivered into the cell type of interest with the gRNA(s) and e.g the Cas9. The repair template must contain the desired alteration as well as additional homologous sequence immediately upstream and downstream of the target (the left and right homology arms).

Prior to the CRISPR system, genome engineering approaches, like zinc finger nucleases (ZFNs) or transcription-activator-like effector nucleases (TALENs), relied upon the use of customizable DNA-binding protein nucleases that required scientists to design and generate a new nuclease-pair for every genomic target. Largely due to its simplicity and adaptability, CRISPR has rapidly become one of the most popular approaches for genome engineering.

Recent studies have demonstrated that the CRISPR-Cas9 system may be employed as a genome editing tool in human cells, mice, zebra fish, *drosophila*, worms, yeast, bacteria, and plants. The system is versatile, even enabling multiplex genome engineering by programming the used endonuclease (e.g. Cas9) to edit several sites in a genome simultaneously by simply using multiple guide RNAs. The easy conversion of Cas9 into a nickase was shown to facilitate homology-directed repair in mammalian genomes with reduced mutagenic activity.

Despite these recent advances in understanding mechanisms of targeted DNA alteration, targeted alteration in plant material is still not always successful or efficient. Indeed available methodology (often optimized for animal, in particular human, cell material) is not always successful or efficient when applied specifically to plant cells. Thus, there is a need for new methods of providing plant cells wherein a targeted alteration has been introduced with a CRISPR-based system and protocol specifically designed for such plant cells. Such method may, preferably, be successfully applied on various plant cells and with a suitable efficiency in comparison to methods known in the art.

In light of this, new compositions, methods and uses for providing plant cells wherein a targeted alteration has been introduced, or for introducing a targeted alteration in the DNA of a plant cell, would be highly desirable. In particular there is a clear need in the art for reliable, efficient, reproducible and in particular targeted compositions, methods and uses that allow for efficient targeted alteration of a DNA molecule in a plant cell. Accordingly, the technical problem underlying the present invention can be seen in the provision of such compositions, methods and uses for complying with any of the aforementioned needs. The technical problem is solved by the embodiments characterized in the claims and herein below.

Recently there have been some reports that Cas9 protein can indeed be used to generate mutations in a plant gene of interest without using DNA constructs (e.g. see Woo et al. 2015. Nat Biotech 33, 1162-1164). These methods are based on the introduction of Cas9 protein and in vitro transcribed sgRNA into plant protoplasts. The present inventors identified that the conditions described in these methods are sub-optimal, and for some species even lethal. The present invention uncovers improved, and in some instances essential, parameters for targeted alteration in plant DNA using Cas9 protein and in vitro transcribed guide RNA, to ensure good protoplast survival and growth.

DESCRIPTION

Drawings and Figures

Embodiments of the invention are further described hereinafter with reference to the accompanying drawings, in which:

FIG. 1 shows the *S. pyogenes* Cas9 ORF (Accession number NC_002737; SEQ ID NO:2). The Transportan sequence is underlined and the protein also includes a 6×HIS sequence tag for simple purification (bold) and a nuclear localization signal to ensure transport of the protein to the nucleus (in italics).

FIG. 2 shows The ORF of a variant with altered codon usage for optimal expression in tomato, *Solanaceae esculentum* of the *S. pyogenes* Cas9 ORF (Accession number NC_002737; SEQ ID NO:3).

FIG. 3 shows a sgRNA (SEQ ID NO: 4) including a putative mutation site in exon 5 (TTACTGCATTCCATACTCGA; SEQ ID NO:1) of the locus 3g095310 of tomato fused to the *Arabidopsis thaliana* U6 polIII promoter sequence. The *A. thaliana* U6 promoter is underlined, the 3g095310 target site sequence is in bold and the remainder of the sgRNA is shown in italics.

FIG. 4 shows the Cas9 protein and the 3g095310 sgRNA were able to digest the PCR product producing fragments of the expected sizes. Therefore, these reagents showed good activity and can be used for mutagenesis experiments. Digestion of a 3g095310 PCR product carrying the putative target site with the Cas9 protein and the 3g095310 sgRNA; Lane 1, 3g095310 PCR product Lane 2, 3g095310 PCR product+Cas9 protein+3g095310 sgRNA.

FIG. 5 shows the detection of indel mutations in 4% of the cloned PCR products, suggesting that the Cas9 protein and sgRNA are able to enter the tomato protoplasts where they form an active nuclease complex that is targeted to the correct genomic site. Indel mutations found in the clones derived from the 3g095310 target site after the transfection of Cas9 protein and 3g095310 sgRNA to tomato protoplasts. The underlined sequence (WT) represents the unaltered target site aligned with the indels found in the individual mutant clones. The dashed represent the number and position of the nucleotides deleted in each clone. The number indicates how many nucleotides have been deleted. The figure includes six sequences, which are identified in descending order as SEQ ID NOs:9-14.

FIG. 6 shows that 3.9% (26 out of 658) contained an indel mutation at the 3g095310 target site. Genotyping of the calli derived from plasmid transfection to protoplasts showed that 2.8% (32 out of 1128) contained a mutation at the 3g095310 target site. Indel mutations found in the calli at the 3g095310 target site after the transfection of Cas9 protein and 3g095310 sgRNA to tomato protoplasts. The underlined sequence (WT) represents the unaltered target site aligned with the indels found in the individual mutant calli. The dashed represent the number and position of the nucleotides deleted in each callus. The number indicates how many nucleotides have been deleted or added (in bold). The majority of calli are heterozygous for the indel mutation. However, some calli contain biallelic mutations (BI) where the same indel mutation is present in both copies of the gene while callus 2C10 (A & B) is biallelic but contains different indel mutations in each gene. The figure includes twenty five sequences, which are identified in descending order as follows: (1) the first sequence is SEQ ID NO:9, (2) the second through 11th sequences are SEQ ID NOs:15-24, (3) the 12th sequence is only 6 nucleotides in length, which is not required to be identified with a sequence identifier, and (4) the thirteenth through 25th sequences are SEQ ID NOs:25-37.

Figure 7:
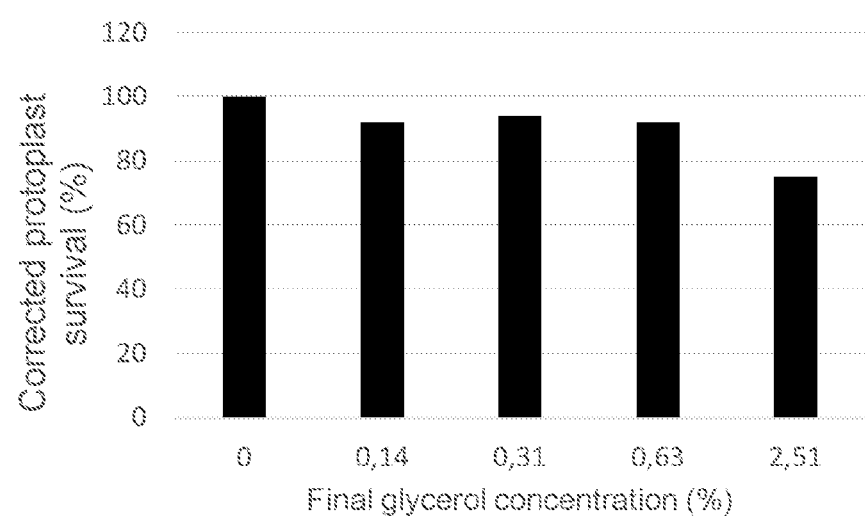

FIG. 7 shows the effect of varying glycerol concentrations on protoplast survival. The final concentration of glycerol (v/v) is shown on the x-axis and the percentage of surviving protoplasts on the y-axis. The control (no added glycerol) is arbitrarily set to 100% and the number of surviving cells in the other samples is shown using this as a reference.

DEFINITIONS

A portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent Office patent file or records, but otherwise reserves all copyright rights whatsoever.

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

"A," "an," and "the": these singular form terms include plural referents unless the content clearly dictates otherwise. Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"And/or": The term "and/or" refers to a situation wherein one or more of the stated cases may occur, alone or in combination with at least one of the stated cases, up to with all of the stated cases.

"Comprising": this term is construed as being inclusive and open ended, and not exclusive. Specifically, the term and variations thereof mean the specified features, steps or components are included. These terms are not to be interpreted to exclude the presence of other features, steps or components.

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

"Exemplary": this terms means "serving as an example, instance, or illustration," and should not be construed as excluding other configurations disclosed herein.

"Plant": this includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grains and the like.

DETAILED DESCRIPTION

It is contemplated that any method, use or composition described herein can be implemented with respect to any other method, use or composition described herein. Embodiments discussed in the context of methods, use and/or compositions of the invention may be employed with respect to any other method, use or composition described herein. Thus, an embodiment pertaining to one method, use or composition may be applied to other methods, uses and compositions of the invention as well.

As embodied and broadly described herein, the present invention is directed to the finding by the inventors that there is an unexpected relationship between the presence of glycerol in the incubation mixture of medium and the efficiency of providing a plant cell having a targeted alteration in a DNA molecule, wherein that method comprises contacting the plant cells with a medium comprising a CAS-protein or CAS-like protein and a CRISPR-CAS system guide RNA (hereafter also referred to as sgRNA, gRNA or guide RNA) in the presence of polyethylene glycol (PEG). A guide RNA is to be understood as a crRNA hybridized to tracrRNA, or a single chain guide RNA as described e.g. Jinek et al. (2012, *Science* 337: 816-820), or single RNA-guide such as for use with Cpf-1.

In other words, it was to the surprise of the current inventors that when plant cells are contacted with an aqueous medium comprising a CAS-protein or CAS-like protein and a sgRNA and PEG with the purpose of introducing said CAS-protein or CAS-like protein and the sgRNA in the plant cell with the purpose of (targeted) altering a DNA molecule in said plant cell, such medium should be substantially free of glycerol. Contrary to this finding, the skilled person is aware that in the art so-called glycerol shocks (using for example substantial amounts of glycerol, for example more than 5, 10 or even 20% (v/v) glycerol) are promoted to improve transfection efficiency (see e.g. Grosjean et al. Biotechnology Letters (2006), 28(22):1827-1833 or Jordan et al. Nucl. Acids Res. (1996) 24 (4): 596-601.doi: 10.1093/nar/24.4.596).

In addition to the finding the aqueous medium contacting the plant cells should be substantially free of glycerol, the current inventors also found that optimal results (e.g. providing plant cells having a targeted alteration in a DNA molecule) are achieved by including several other steps and factors, as will be detailed below.

Therefore, according to a first aspect there is provided for a method of providing plant cells having a targeted alteration in a DNA molecule, the method comprising contacting a population of plant cells comprising a DNA molecule, the DNA molecule having a target sequence, with an aqueous medium, wherein the aqueous medium comprises a CRISPR associated protein (CAS protein) or a CAS-like protein, and a CRISPR-CAS system guide RNA that hybridizes with the target sequence, and wherein the aqueous medium comprises polyethylene glycol (PEG) and is substantially free of glycerol.

In the method a population of plant cells is contacted with an aqueous medium comprising a CAS protein or CAS-like protein and a CRISPR-CAS system guide RNA.

Although not limited thereto, the plant cells are preferably contacted for a period of at least 5 minutes, for example for a period of between 5 minutes and 24 hours, or between 5 minutes and 6 hours, or between 5 minutes and 60 minutes, or between 5 minutes and 30 minutes, or between 5 minutes and 25 minutes. Contacting may be at any suitable temperature, for example a temperature between 4 degrees Celsius and 40 degrees Celsius, preferably between 10 degrees Celsius and 30 degrees Celsius, for example at room temperature.

As explained in the background of the invention part herein, the skilled person is well aware of the CRISPR or CRISPR-CAS system and its use in altering DNA present in a cell. The CAS-protein or CAS-like protein provides for endonuclease activity, in combination with the system guide RNA (sgRNA) that is designed to specifically target a sequence present in the DNA molecule in the plant cell, and hybridize with said target sequence in the DNA molecule once introduced in the plant cell. After hybridization of the CAS-protein (e.g. CAS9)-sgRNA complex to the DNA, the endonuclease activity of the CAS protein may introduce a double-strand break at the target site in the DNA molecule.

The skilled person knows how to prepare the different component of the CRISPR-CAS system. In the prior art numerous reports are available on its design and use. See for example the recent review by Haeussler et al (J Genet Genomics. (2016)43(5):239-50. doi: 10.1016/j.jgg.2016.04.008.) on the design of sgRNA and its combined use with the CAS-protein CAS9 (originally obtained from *S. pyogenes*).

Moreover, the skilled person will understand that next to the specific requirement defined herein with respect to the medium, it may be any suitable medium. For example, the medium has preferably a pH value of between 5-8, preferably between 6-7.5.

Next to the presence in the aqueous medium of the CAS-protein or the CAS-like protein and the sgRNA, the medium comprises polyethylene glycol. Polyethylene glycol (PEG) is a polyether compound with many applications from industrial manufacturing to medicine. PEG is also known as polyethylene oxide (PEO) or polyoxyethylene (POE). The structure of PEG is commonly expressed as H—(O—CH2-CH2)n-OH. Preferably, the PEG used is an oligomer and/or polymers, or mixtures thereof with a molecular mass below 20,000 g/mol.

PEG-mediated gene transformation has been known since 1985. The first method for plant protoplast transformation utilized PEG (Krens et al. (1982) Nature 296: 72-74; Potyrykus et al. (1985) Plant Mol. Biol. Rep. 3:117-128; Negrutiu et al. (1987) Plant Mol. Biol. 8: 363-373). The technique is applicable to protoplasts from many different plants (Rasmussen et al. (1993) Plant Sci. 89: 199-207). PEG is thought to stimulate transformation by precipitating the DNA, in the presence of divalent cations, onto the surface of the plant protoplasts from where it then becomes internalized (Maas & Werr (1989) Plant Cell Rep. 8: 148-151). None of the above describe prior art has contemplated the use of PEG transformation to introduce into the plant cells the sgRNA and the CAS protein and/or CAS-like protein with the purpose of targeted alteration of DNA in the plant cell, and in particular that in such use, the aqueous medium should be substantially free of glycerol.

As explained herein, to the surprise of the inventors, the aqueous medium should be substantially free of glycerol. Glycerol is a simple polyol compound. It is a colorless, odorless, viscous liquid that is sweet-tasting and generally considered non-toxic. Glycerol is commonly used in buffers, media, and the like, used in biological sciences. Glycerol is used to stabilize proteins in solutions and/or as an anti-freeze agent, so that the proteins and enzymes can be kept at low temperature. For example, CAS9 protein is commonly sold in the form of a storage solution comprising high levels of glycerol (e.g. up to 50%; see for example, www.neb.com/products/m0386-cas9-nuclease-s-*pyogenes*#pd-description). Thus whereas glycerol is used to stabilize proteins in solution, it was found that in the context of the current invention, the presence of such glycerol in the aqueous medium comprising the CAS-protein or CAS-like protein reduced overall efficacy of the method (e.g. in providing plant cell having a targeted alteration in a DNA molecule). Indeed when glycerol concentration is too high in the aqueous medium, results showed that no plant cell having a targeted alteration in a DNA molecule may be obtained at all.

The skilled person understands that the allowable concentration of glycerol may, to some extent, depend on the experimental settings and, based on the current disclosure, the skilled person will have no problems determining such maximal allowable concentration, and above which the efficacy of the method of the current invention is reduced.

The skilled person understand that within the context of the current invention, the targeted alteration in the DNA molecule in the plant may be any type of alteration such as a deletion of one or more nucleotide(s), insertion of one or more nucleotide(s) and/or substitution of one or more nucleotide(s) as the target location in the DNA molecule, including so-called INDEL mutations (i.e. mutations resulting in an insertion of nucleotides or a deletion of nucleotides or both, and which may results in a net change in the total number of nucleotides).

In addition to the finding that the medium used in the present invention needs to be substantially free of glycerol, it was found that in combination therewith desirable results are obtained when the amount of cells that are contacted with the aqueous medium comprising the CAS-protein and/or CAS-like protein, the sgRNA and the PEG amounts to about 10000-2 000 000 plant cells per milliliter of aqueous medium. Thus, although the amount of cells may be varied and may be outside the given range, in a preferred embodiment the amount of cells per millimeter of the aqueous medium is between 10 000 and 2 000 000 plant cells. The skilled person knows how to provide for such number of cells.

The cells are preferably provided as cells that are detached from each other, i.e. as single cells, although some cells in the population may be connected to each other, and may form small lumps of cells. Again, the skilled person knows how to provide a population of cells wherein the cells are, at least in majority, in a single cell form, i.e. in a form wherein the majority of the cells are not connected to each other.

As explained herein elsewhere, the skilled person understands that the method of the current invention may be applicable to different plant cells, for example plant cells of different plant species. Indeed it is contemplated the invention disclosed herein may be applicable to plant cells of a wide range of plants, both monocots and dicots. Non-limiting examples include plant cells from the Cucurbitaceae, Solanaceae and Gramineae, maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), Brassica spp. (e.g. *B. napus, B. juncea, B. oleracea, B. rapa*, etc), sunflower (*Helianthus annus*), safflower, yam, cassava, alfalfa (*Medicago sativa*), rice (*Oryza* species, e.g. *O. sativa indica* cultivar-group or *japonica* cultivar-group), forage grasses, pearl millet (*Pennisetum* spp. e.g. *P. glaucum*), tree species (*Pinus*, poplar, fir, plantain, etc), tea, *coffea*, oil palm, coconut, vegetable species, such as pea, zucchini, beans (e.g. *Phaseolus* species), cucumber, artichoke, asparagus, broccoli, garlic, leek, lettuce, onion, radish, lettuce, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia, Chrysanthemum, Lily, Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*), or model organisms, such as *Arabidopsis thaliana*.

However, in a preferred embodiment the plant cells are plant cells obtained from tomato.

According to another preferred embodiment, the population of plant cells is a population of plant protoplasts, preferably tomato plant protoplasts. The skilled person may provide plant protoplast by using methods available for the preparation of plant protoplast for various plants. For example, plant protoplasts may be prepared by treating a whole plant, a part of the same or plant cells with enzymes such as cellulose or pectinase or by an appropriate mechanical means to remove the cell wall. The resultant plant protoplasts are than placed in an aqueous solution containing an osmotic pressure control agent in order to maintain them in a stable form (see for example Reusink et al. Science (1966) 154 (3746): 280-281 DOI: 10.1126/science.154.3746.280 or Muhlbach et al. Planta (1980)148 (1): 89-96).

Likewise it was found that, next to the aqueous medium used in the method of the invention should be substantially free of glycerol, should preferably have the above disclosed amounts of plant cells or plant protoplasts, the concentration and ratio of the CAS-protein or CAS-like protein and the sgRNA is preferably within certain ranges.

In particular, desirable results are obtained when the aqueous medium aqueous medium comprising the population of plant cells comprises 2-80 nanomolar (nM) CAS-protein or CAS-like protein. Thus were the concentration may, for example, vary between 1 and 200 nM, in a preferred embodiment the concentration is between 2-80 nM, for example between 5-70 nM, between 10-50 nM or between 20-40 nM.

The terms CAS-protein or CAS-like protein refer to CRISPR related proteins and includes but is not limited to CAS9, CSY4, dCAS9 (e.g. CAS9_D10A/H820A), nickases (e.g. CAS9_D10A, CAS9_H820A or CAS9_H839A) and dCAS9-effector domain (activator and/or inhibitor domain) fusion proteins (e.g. CAS9 or CAS-like molecules fused to a further functional domain such as a deaminase domain), and other example, such as Cpf1 or Cpf1_R1226A and such as for example described in WO2015/006747. Mutants and derivatives of Cas9 as well as other Cas proteins can be used in the methods disclosed herein. Preferably, such other Cas proteins have endonuclease activity and are able to recognize a target nucleic acid sequence when in a plant cell in the presence of an sgRNA that is engineered for recognition of the target sequence. The CAS-protein or CAS-like protein is preferable the CAS9 protein of Cpf1.

The Cas9 protein is widely commercial available, as well as modified versions thereof (and which are also contemplated as CAS protein within the context of the current invention). The Cas9 protein has (endo)nuclease activity and is able to produce a specific DNA double strand break (DSB) at the target sequence in the pathogen genome which then becomes degraded. Indeed, it has been shown that the Cas9 protein (nuclease), tracrRNA and crRNA (the components of the CRISPR system) or the sgRNA (the chimeric fusion of the tracrRNA and crRNA) targeting a genomic sequence creates targeted DSBs at the genomic target sequence that is often misrepaired by the cellular DNA machinery, resulting in a small insertion or deletion (INDEL) (Feng et al. (2013) Cell Res. 1: 4; Li et al. (2013) Nat. Biotech. 31: 689-691; Nekrasov et al. (2013) Nat. Biotech. 31: 691-693; Shan et al. (2013) Nat. Biotech. 31: 686-688).

Cpf1 is a single RNA-Guided Endonuclease of a Class 2 CRISPR-Cas System (see e.g. Cell (2015) 163(3):759-771). Cpf1 is a single RNA-guided endonuclease lacking tracrRNA, and it utilizes a T-rich protospacer-adjacent motif. Cpf1 cleaves DNA via a staggered DNA double-stranded break. Cpf1 has shown to have efficient genome-editing activity in human cells. Cpf1 may thus be used as an alternative CAS-protein.

CAS or CAS-like protein may be, but is no limited to, selected from the group consisting of: Cas9 from *Streptococcus pyogenes* (e.g. UniProtKB—Q99ZW2), Cas9 from *Francisella tularensis* (e.g. UniProtKB—A0Q5Y3), Cas9 from *Staphylococcus aureus* (e.g. UniProtKB—J7RUA5), Cas9 from *Actinomyces naeslundii* (UniProtKB—J3F2B0), Cas9 from *Streptococcus thermophilus* (e.g. UniProtKB—G3ECR1; UniprotKB—Q03J16; Q03LF7), Cas9 from *Neisseria meningitidis* (e.g. UniProtKB—C9X1G5; UniProtKB—A1IQ68); *Listeria innocua* (e.g. UniProtKB—Q927P4); Cas9 from *Streptococcus mutans* (e.g. UniProtKB—Q8DTE3); Cas9 from *Pasteurella multocida* (e.g. UniProtKB—Q9CLT2); Cas9 form *Corynebacterium diphtheriae* (e.g. UniProtKB—Q6NK13); Cas9 from *Campylobacter jejuni* (e.g. UniProtKB—Q0P897), Cpf1 from *Francisella tularensis* (e.g. UniProtKB—A0Q7Q2), Cpf1 from Acidaminococcus sp. (e.g. UniProtKB—U2UMQ6), any orthologue thereof or any CRISPR associated endonuclease derived therefrom.

As mentioned herein, also the concentration of the CRISP-CAS system guide RNA (or sgRNA), is, within the context of the invention disclosed herein, preferably within certain ranges. More in particular it was found that using a concentration of 30-600 nanomolar of the CRISPR-Cas system guide RNA in the aqueous medium improves the results obtained (e.g. in providing plant cells having a targeted alteration in a DNA molecule). Thus, for example, a concentration of 10-1000 nM sgRNA (total concentration in case more than one different sgRNA's are used simultaneously used in the of the invention) may be used, but preferable the concentration is between 30-600 nM, for example between 50-400 nM, for example, between 100-300 nM, for example, between 150-250 nM.

According to another preference, the molar ratio between the CAS-protein or CAS-like protein and CRISPR-Cas system guide RNA in the aqueous medium is from 1:300 to 8:3, preferably the molar ratio is 1:20. For example, the molar ratio may from 1:1-1:50, or from 1:5-1:30, or from 1:1 to 8:3, and any other ratio within these preferred ratio's.

Preferably the concentration and ratio of the CAS-protein or CAS-like protein and the sgRNA is within both the given concentration ranges and the given molar ratio's.

As detailed herein, the aqueous medium used to contact the cells should be substantially free of glycerol.

In a preferred embodiment, the aqueous medium comprising the population of plant cells comprises less than 0.1% (v/v) glycerol, preferably the aqueous medium is free of (detectable) glycerol. In other words, the end concentration glycerol in de aqueous medium comprising the population of plant cells is preferably less than 0.1% (v/v), for example, less than 0.09%, 0.08%, 0.07%, 0.06%, 0.05%, 0.04%, 0.03%, 0.02%, 0.01%, 0.09, 0.08, 0.07, 0.06, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% (v/v) glycerol. Optionally, the aqueous medium comprising the population of plant cells is completely free of glycerol.

As detailed herein, the aqueous medium that is substantially free of glycerol, comprises, next to the CAS-protein or CAS-like protein and at least one sgRNA (in principal more than one type of sgRNA may be used in the same experiment, for example aimed at two or more different target sequences, or even aimed at the same target sequence), polyethylene glycol (PEG).

Within the context of the current invention it was found that preferably the concentration of the PEG is within certain ranges. In particular, the aqueous medium comprising the population of plant cells comprises 100-400 mg/ml PEG. So the final concentration of PEG is between 100-400 mg/ml, for example, between 150 and 300 mg/ml, for example between 180 and 250 mg/ml. A preferred PEG is PEG 4000 Sigma-Aldrich no. 81240. (i.e. having a average Mn 4000 (Mn, the number average molecular weight is the total weight of all the polymer molecules in a sample, divided by the total number of polymer molecules in a sample). Preferably the PEG used as a Mn of about 1000-10 000, for example between 2000-6000).

As already detailed herein, in a highly preferably embodiment, there is provided for the method off the invention wherein the aqueous medium comprising the plant cells comprises:
  2-80 nanomolar (nM) CAS-protein or CAS-like protein;
  30-600 nanomolar (nM) CRISPR-Cas system guide RNA;
  less than 0.1% (v/v) glycerol;
  100-400 mg/ml PEG, and
  10.000-2.000.000 plant cells/ml.

It was found that this combination of parameters is surprisingly effective in providing plant cells having a targeted alteration in a DNA molecule. Indeed it was found that deviations of the above parameters may reduce efficiency and/or efficacy.

In addition to the above, it was found that efficiency and/or efficacy of the method of the invention is improved when PEG is added to the aqueous medium after the CAS-protein or CAS-like protein and the CRISPR-Cas system guide RNA are provided to the medium. Thus, whereas PEG may be added to the aqueous medium before the CAS-protein or CAS-like protein and the CRISPR-Cas system guide RNA are provided to the medium, preferably the aqueous medium is first provided with the CAS-protein or CAS-like protein and the CRISPR-Cas system guide RNA, and after which the PEG is provided to the medium. Preferably the time between adding the CAS-protein or CAS-like protein and the CRISPR-Cas system guide RNA and the PEG is between 5 seconds and 10 minutes, but may be shorter or longer, if so desired.

According to a further preference, there is provided that the method of the invention further comprises contacting the plants cells with a DNA oligonucleotide or DNA polynucleotide comprising the desired alteration to be introduced in the DNA molecule in the plant.

While NHEJ-mediated DSB repair may be imperfect and often results in disruption of the open reading frame of the gene, homology directed repair may be used to generate specific nucleotide changes ranging from a single nucleotide change to large insertions. For this use is made of a DNA "repair template" containing the desired sequence and which must be delivered into the cell type of interest with the gRNA(s) and CAS protein or CAS like protein.

The repair template must contain the desired alteration as well as additional homologous sequence immediately upstream and downstream of the target (the so-called left & right homology arms). The length and binding position of each homology arm is dependent on the size of the change being introduced. The repair template can be a single stranded oligonucleotide (an oligonucleotide having any length of between 6 and 250 nucleotides), double-stranded oligonucleotide, or double-stranded DNA plasmid depending on the specific application.

According to further preferred embodiment, there is provided for a method of the invention wherein the population of plant cells is further cultivated, i.e. after being contacted with the aqueous medium, as detailed herein, in the presence of feeder plant cells, preferably wherein the feeder plant cells are plant protoplasts, preferably wherein the feeder plant cells are of the same plant species as the population of plant cells, preferably wherein the feeder plant cells are provided in the form of a feeder disc, preferably containing 50000-250000 feeder plant cells.

The skilled person knows how to cultivate protoplast in the presence of feeder cells, for example as detailed in the examples. It was found that the presence of feeder cells during the cultivation period after the plant cells have been contacted with the aqueous medium that is substantially free of glycerol, but comprises the CAS/CRISPR system components and the PEG, may increase overall efficacy and/or efficacy of the method according to the invention. This is in particular true when the feeder cells are of the same plant species as the population of plant cells that was contacted with the CRISPR/CAS system in the aqueous medium, and in particular when an amount of 50000-250000 feeder plant cells per feeder disc is used (normally one feeder disc per experiment is used).

The skilled person knows other techniques on how to cultivate protoplast in the presence of feeder cells, for example as detailed in Plant Science Letters (1984) 33 (3): 293-302; doi:10.1016/0304-4211(84)90020-8 or described in various handbooks including Plant Cell and Tissue Culture (ISBN 0-7923-2493-5; edited by Vasil and Thorpe; Kluwer Academic Publishers).

Also contemplated is for a method of the invention wherein the individual protoplasts from the population of plant cells are further cultivated into plant calli, plant cells comprising a plant cell wall, and/or plants.

The method of the invention is in particular suitable for targeting, within the DNA molecule, a nucleotide sequence, for example gene or promoter, that confers one or more of the following traits: herbicide tolerance, drought tolerance, male sterility, insect resistance, abiotic stress tolerance, modified fatty acid metabolism, modified carbohydrate metabolism, modified seed yield, modified oil percent, modified protein percent, and resistance to bacterial disease, fungal disease or viral disease, although it may be used to target any kind of sequence within the DNA molecule.

In another preferred embodiment there is provided for the method of the invention wherein the aqueous medium does not comprise any plasmid or vector material, in particular any plasmids material or vector material that encodes for a CAS protein and/or CAS like protein. Having such vector present in the medium may case the undesired introduction thereof in the DNA molecule in the plant or plant cell.

According to another aspect there is provided for the use of an aqueous medium comprising 2-80 nanomolar (nM) CAS-protein or CAS-like protein, 30-600 nanomolar (nM) CRISPR-Cas system guide RNA, less than 0.1% (v/v) glycerol, and 100-400 mg/ml PEG in providing plant cells having a targeted alteration in a DNA molecule./pct The skilled person understands that with respect to the various limitations and preferences disclosed herein with respect to the method of the invention, these likewise apply to the above use of the aqueous medium.

Also provided is for the protoplast, population of protoplasts, plant cells comprising a plant cell wall, plant, or seed thereof, obtained with the method or use according to the invention.

According to another aspect of the invention there is provided for a composition, preferably an aqueous composition, comprising
- CAS-protein or CAS-like protein, preferably 2-80 nanomolar (nM) CAS-protein or CAS-like protein;
- CRISPR-Cas system guide RNA, preferably 30-600 nanomolar (nM) CRISPR-Cas system guide RNA;
- less than 0.1% (v/v) glycerol, preferably no glycerol; and
- 100-400 mg/ml PEG.

The skilled person understands that with respect to the various limitations and preferences disclosed herein with respect to the method of the invention and use of the invention, these likewise apply to the above composition.

For example, in a preferred embodiment, the composition further comprises 10.000-2.000.000 plant cells/ml.

The skilled person understands that the method disclosed herein is also a method of targeted alteration of a DNA molecule in a plant cell. Thus also provided is a method of targeted alteration of a DNA molecule in a plant cell, the method comprising contacting a population of plant cells comprising the DNA molecule to be targeted, the DNA molecule having a target sequence, with an aqueous medium, wherein the aqueous medium comprises a CRISPR associated protein (CAS protein) or a CAS-like protein, and a CRISPR-Cas system guide RNA that hybridizes with the target sequence, and wherein the aqueous medium comprises polyethylene glycol (PEG) and is substantially free of glycerol.

The skilled person understands that with respect to the various limitations and preferences disclosed herein with respect to the method described above, these likewise apply to the method of targeted alteration of a DNA molecule in a plant cell.

Finally, the skilled person understands that the method disclosed herein is also a method of introducing a CRISPR associated protein (CAS protein) or a CAS-like protein, and a CRISPR-Cas system guide RNA in a plant cell. Therefore, also provided is a method of introducing a CRISPR associated protein (CAS protein) or a CAS-like protein, and a CRISPR-Cas system guide RNA, the method comprising contacting a population of plant cells with an aqueous medium, wherein the aqueous medium comprises a CRISPR associated protein (CAS protein) or a CAS-like protein, and a CRISPR-Cas system guide RNA, and wherein the aqueous medium comprises polyethylene glycol (PEG) and is substantially free of glycerol.

The skilled person understands that with respect to the various limitations and preferences disclosed herein with respect to the method described above, these likewise apply to the method of method of introducing a CRISPR associated protein (CAS protein) or a CAS-like protein, and a CRISPR-Cas system guide RNA in a plant cell.

Having now generally described the invention, the same will be more readily understood through reference to the following examples which is provided by way of illustration and is not intended to be limiting of the present invention.

EXAMPLES

Example 1—Induction of Indels at the Tomato 3g095310 Locus Using Cas9 Protein and In Vitro Transcribed sgRNA Materials and Methods
Constructs The *S. pyogenes* Cas9 ORF (FIG. 1) (Accession number NC_002737) was synthesized with a nuclear localization signal and a codon usage optimized for *E. coli* and was then cloned into the expression vector pET28 (Invitrogen) resulting in the fusion of a 6×HIS epitope at the N terminus of the protein which can be used for purification. This was then transformed to the *E. coli* strain BL21 (DE3) (Invitrogen) for protein production.

The *S. pyogenes* Cas9 ORF (Accession number NC_002737) was also used to design a variant that had altered codon usage for optimal expression in tomato, *Solanaceae esculentum*. The resulting ORF is shown in FIG. 2. The ORF was then synthesized (www.geneart.com) flanked by both XhoI (5') and SacI (3') sites and cloned into a plasmid.

The Cas9 ORF fragment was then isolated from this plasmid after digestion with XhoI and SacI. The constitutive cauliflower mosaic virus 35S promoter present on the vector pKG7381 was used to express the Cas9 ORF in tomato protoplasts. Plasmid pKG7381 carries a 6×HIS tagged version of green fluorescent protein (GFP) flanked by XhoI and SacI sites. The GFP ORF in pKG7381 was replaced by the Cas9 ORF using the XhoI and SacI sites, resulting in the construct pKG7230 that carries the Cas9 ORF with a nuclear localization sequence (NLS) and 6×HIS tag translationally fused at its N-terminus. This vector can be used for the expression of the Cas9 protein in plant cells.

Protein Expression and Purification

The Cas9 expression strain was grown in LB medium supplemented with kanamycin (50 µg/ml) to an OD600=0.6 and IPTG was then added a final concentration of 1 mM to induce protein production. These cultures were then grown overnight in a shaker at 22° C. for optimal protein expression. The recombinant proteins were then purified using the Ni-NTA Spin Kit (Qiagen) following the manufacturers protocol. Protein production was then confirmed by separation of the purified proteins on a 10% polyacrylamide gel (Invitrogen) followed by Coomassie staining. The purified proteins were then dialyzed against a buffer (G) consisting of 20 mM HEPES, 150 mM KCl, 1 mM DTT and 10% glycerol using 20K Slide-a-Lyzer dialysis cassettes (Thermo Scientific) overnight at 4° C. The protein was then removed from the cassette and passed over an Amicon Ultra-4 100K Centrifugation Filter (Millipore). The protein on the filter was washed with 1×PBS buffer (NaCl, 80 g/l; KCl, 2 g/l; $Na_2HPO_4$, 14.4 g/l; $KH_2PO_4$, 2.4 g/l; pH7.4) and then finally washed from the filter using 200 µl 1×PBS buffer. The concentration of the Cas9 protein was the quantified on a 10% polyacrylamide gel using a commercial Cas9 protein (M0641, New England Biolabs, 166 ng/µl) as a standard followed by Coomassie gel staining.

sgRNA Synthesis for the Tomato Locus 3g095310

Analysis of the locus 3g095310 of tomato identified a putative mutation site in exon 5 (TTACTGCATTCCATACTCGA; SEQ ID NO:1). A sgRNA including this sequence was then synthesized fused to the *Arabidopsis thaliana* U6 polIII promoter sequence (FIG. 3). This plasmid (KG9492) was then used as a template for PCR with the primers T7-3g095310F (5'-GGATCCTAATACGACTCAC-TATAGTTACTGCATTCCATACTCGA-3'; SEQ ID NO:5) and sgRev (5'-AAAAAAAGCACCGACTCGG-3'; SEQ ID NO:6) resulting in a product with the sgRNA sequence fused to the T7 polymerase promoter. The PCR products were then precipitated and purified over Probe Quant G50 Micro column (GE Healthcare) and then used as a template for in vitro RNA synthesis using the Ampliscribe T7 Flash Transcription Kit (Epicentre). The sgRNAs was then purified and concentrated using the ssDNA/RNA Clean and Concentrator kit (ZymoResearch) and quantified on the Qubit.

Cas9 Protein and 03g095310 sgRNA In Vitro Testing

Primers were designed (forward, 5'-aaggtgaagggggtaaaatgg-3' (SEQ ID NO:7); reverse, 5'-gaaggtgaaggggtaaaatgg-3' (SEQ ID NO:8)) that amplify a 536 bps region of this locus including the putative mutation site. This PCR product was amplified from tomato genomic DNA and then used in a digestion reaction with the purified Cas9 protein and transcribed 3g095310 sgRNA. For the reaction, 300 ng of PCR product was incubated in a 10 µl reaction with 160 ng Cas9 protein, 200 ng 3g095310 sgRNA and 1 µl 10× reaction buffer (20 mM HEPES, 100 mM NaCl, 5 mM MgCl2, 0.1 mM EDTA, pH6.5) for 1 hr at 37° C. 1 µl of RNaseA (4 mg/ml) was then added and after 15 minutes the samples were analyzed on a agarose gel (FIG. 4). As shown in the figure the Cas9 protein and the 3g095310 sgRNA were able to digest the PCR product producing fragments of the expected sizes. Therefore, these reagents showed good activity and can be used for mutagenesis experiments.

Tomato Protoplast Isolation and Transfection

In vitro shoot cultures of *Solanum lycopersicon* var Moneyberg were maintained on MS20 medium with 0.8% agar in high plastic jars at 16/8 h photoperiod of 2000 lux at 25° C. and 60-70% RH. Young leaves (1 g) were gently sliced perpendicularly to the mid nerve to ease the penetration of the enzyme mixture. Sliced leaves were transferred to the enzyme mixture (2% Cellulase Onozuka RS, 0.4% Macerozyme Onozuka R10 in CPW9M) and cell wall digestion was allowed to proceed overnight in the dark at 25° C. The protoplasts were filtered through a 50 µm nylon sieve and were harvested by centrifugation for 5 minutes at 800 rpm. Protoplasts were resuspended in CPW9M (Frearson, 1973) medium and 3 mL CPW18S (Frearson, 1973) was added at the bottom of each tube using a long-neck glass Pasteur pipette. Live protoplasts were harvested by centrifugation for 10 minutes at 800 rpm as the cell fraction at the interface between the sucrose and CPW9M medium. Protoplasts were counted and resuspended in MaMg (Negrutiu, 1987) medium at a final density of $10^6$ per mL.

Two different reagent mixtures were made. The first consisted of 80 pmol of the Cas9 protein in buffer G (20 mM HEPES pH7.5, 150 mM KCl, 1 mM DTT, 10% glycerol) and 600 pmol of the 3g095310 sgRNA. The second reagent mixture was made up of 8 pmol Cas9 protein resuspended in 1×PBS buffer and 150 pmol 3g095310 sgRNA. As a control we also performed transfections using 4 pmol of plasmid KG7230 (35::Cas9) together with 6 pmol of plasmid KG9492 (U6p::3g095310 sgRNA). These reagent mixtures were added to 500 µL (500000 protoplasts) of the protoplast suspension and 500 µL of PEG solution (400 g/l poly (ethylene glycol) 4000, Sigma-Aldrich #81240; 0.1M $Ca(NO_3)_2$) was then added and the transfection was allowed to take place for 20 minutes at room temperature. Then, 10 mL of 0.275 M $Ca(NO_3)_2$ solution was added and thoroughly, but gently mixed in. The protoplasts were harvested by centrifugation for 5 minutes at 800 rpm and resuspended in 9M culture medium at a density of $0.5×10^6$ per ml and transferred to a 4 cm diameter petri dish and an equal volume of 2% alginate solution (20 g/l Alginate-Na (Sigma-Aldrich #A0682), 0.14 g/l $CaCl_2.2H_2O$, 90 g/l mannitol) was added. Then 1 ml aliquots (125000 transfected protoplasts) were spread over Ca-Agar plates (72.5 g/l mannitol, 7.35 g/l $CaCl_2.2H_2O$, 8 g/l agar, pH5.8) and allowed to polymerize for 1 hour. To improve protoplast survival we also produced "feeder" discs containing 200000 tomato protoplasts (Moneyberg variety) that had not been transfected but were embedded in alginate using the same protocol. For protoplast cultivation 4 ml of K8p (Kao, 1975) culture medium was added to a 4 cm tissue culture dish containing both a feeder disc with a disc of transfected protoplasts placed on top of this. To detect indels in tomato protoplasts the disc of transfected protoplasts was removed from the dish after 48 hours and the alginate was dissolved and the protoplasts were isolated. For the regeneration of calli, the discs were incubated together for 21 days at 28° C. in the dark. After this period the dics of transfected protoplasts were transferred to solid GM medium (Tan, Plant Cell Reports 6(3), 172, 1987 supplemented with 1 mg·l$^{-1}$ zeatin and 0.2 mg·l$^{-1}$ GA3 and grown for a further 3 weeks at which point the calli were approximately 0.3 mm in size. The alginate was then dissolved and the calli were spread on a fresh plate of GM medium and allowed to grow until they were approximately 1.5 mm, at which point they were once again transferred to fresh medium and then genotyped after a further 14 days.

Genotyping Protoplasts and Calli

Tomato protoplasts that had been transfected with the Cas9 protein and 3g095310 sgRNA were cultivated for 48 hours and then collected after removal of the alginate. Total genomic DNA was then isolated from the samples using the DNeasy Plant Mini Kit (Qiagen) and used as a template for the amplification of the 3g095310 target site using the gene specific primers. This 536 bps PCR fragment was then purified using the DNeasy PCR purification kit and then ligated into a plasmid using the Zero Blunt PCR Cloning Kit (Invitrogen). The ligation was transformed to chemically competent *E. coli* cells which were then plated on solid LB medium containing kanamycin (50 µg/ml). PCR was then performed on 96 individual colonies using the M13 forward and M13 reverse primers and these PCR products were then directly digested with the restriction enzyme XhoI. The 3g095310 sgRNA induces indels at this XhoI site and thus the loss of this site, as scored by lack of digestion, is a simple method of genotyping a large number of clones to determine the efficiency of indel formation. The PCR products that were resistant to XhoI digestion were then sequenced to confirm the presence of an indel. Calli were genotyped directly using the direct PCR kit (Phire Plant Direct PCR kit, Thermo Scientific) and the 3g095310 gene specific primers described above. The resulting PCR products were then directly digested with XhoI and analysed on an agarose gel.

Callus Regeneration

Calli were transferred to MS medium supplemented with 2 mg·l$^{-1}$ zeatin and 0.1 mg·l$^{-1}$ IAA media after which regenerated tomato plantlets were rooted on MS medium supplemented with 0.5 mg·l$^{-1}$ IBA before transfer to the greenhouse.

Results

Our experimental setup uses 8 pmol of Cas9 protein resuspended in PBS buffer, 150 pmol of in vitro transcribed sgRNA and a feeder disc containing 200000 protoplasts to ensure survival of the transfected protoplasts. Genomic DNA from tomato protoplasts treated with our protocol was isolated 48 hours after the transfection and was used as a template to amplify the 3g095310 target site. These PCR products were then cloned and genotyped to identify clones that contained indel mutations. We detected indel mutations in 4% of the cloned PCR products (FIG. 5), suggesting that the Cas9 protein and sgRNA are able to enter the tomato protoplasts where they form an active nuclease complex that is targeted to the correct genomic site. The next step was to demonstrate that our protocol would enable us to generate calli with indel mutations in the 3g095310 target site and that these calli could be regenerated into plants that also carried the expected indel mutation. Therefore, we repeated the protoplast transfection using our protocol and then regenerated calli that were then genotyped for the presence of the indel. We were also interested in determining how efficient the protein based method was at creating indel mutations compared with the more established method that involves the transfection of plasmids carrying expression cassettes for the Cas9 protein and the sgRNA. When we genotyped calli derived from Cas9 protein/sgRNA transfection to protoplasts we found that 3.9% (26 out of 658) contained an indel mutation at the 3g095310 target site (FIG. 6). Genotyping of the calli derived from plasmid transfection to protoplasts showed that 2.8% (32 out of 1128) contained a mutation at the 3g095310 target site. This demonstrates that the method using protein is equivalent to the more established method utilizing plasmids and that it has no inherent disadvantages. We were able to regenerate tomato plants from calli obtained from both the protein and the plasmid methods. These plants were genotyped and were found to contain the same mutations that had been present in the original callus.

During the development of this protocol we discovered several parameters that were important for optimizing the results obtained, in particular to ensure the survival of the transfected protoplasts and therefore the successful recovery of edited calli.

Firstly, we surprisingly found that the presence of glycerol in the Cas9 protein buffer had a large negative effect on protoplast survival and should be kept as low as possible, preferably below the level of 0.1% (v/v) in the transfection mixture (end concentration).

Second, the amount and ratio of Cas9 protein and sgRNA (for example added at a molar ratio of 1::20) added to the transfection influence the outcome. It was surprisingly found that for the best experimental results these may fall within certain preferred ranges. For the CAS protein (here CAS9) between 2-80 nanomolar (nM) pmol may be used and for the sgRNA a range of 30-600 nanomolar (nM) was found to be optimal.

The amount of protoplasts in the transfection may preferably be in the range of 10000-2000000 cells/ml. Finally, optimal results were obtained when a feeder disc (preferably containing 50000-250000 protoplasts) was used to improve survival of the transfected protoplasts. Indeed the best results, providing the most plants containing indels at the target site were obtained when all of these optimal conditions were used combined in a single transfection. The skilled person understand that experiments, using the above combination of optimal conditions, in other plants may provide similar results.

Example 2—Effect of Glycerol Concentration on Tomato Protoplast Survival

Tomato protoplasts were isolated from leaves and re-suspended in medium to a density of $1 \times 10^6$ per ml. Subsequently, we took 0.5 ml of protoplasts and added 1 µg of Cas9 protein, 5 µg of a sgRNA and varying amounts of 60% glycerol (FIG. 7). PEG was then added to each sample (500 µl to give a final volume of 1 ml) and a standard transfection was performed (see Example 1). The protoplasts were then re-suspended in alginate solution that was then allowed to polymerize and the protoplasts were incubated for 72 hours in medium. The alginate discs containing the protoplasts were then incubated with the vital dye FDA and the number of living protoplasts in each sample was calculated.

Results

The results show the addition of 0.14% glycerol during transfection already has a negative effect on protoplast survival at the single cell level after only 36 hours cultivation. Given our previous observation that addition of small amounts of glycerol to the transfection can severely inhibit callus formation we expect that even a small decrease in cell survival will also inhibit cell division dramatically to the point where no calli will be obtained from the experiment.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding patent applications, patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The invention claimed is:

1. A method of providing plant cells having a targeted alteration in a DNA molecule, the method comprising contacting a population of plant cells comprising a DNA molecule having a target sequence with an aqueous medium comprising a CRISPR associated protein (CAS protein) or a CAS-like protein, a CRISPR-Cas system guide RNA that hybridizes with the target sequence, and polyethylene glycol (PEG), wherein the end concentration of glycerol in the aqueous medium comprising the population of plant cells is less than 0.01% (v/v) glycerol.

2. The method according to claim 1, wherein the population of plant cells is contacted with the aqueous medium such that the aqueous medium comprising the population of plant cells comprises 10,000-2,000,000 plant cells/ml.

3. The method according to claim 1, wherein said plant cells are tomato cells.

4. The method according to claim 1, wherein the population of plant cells is a population of plant protoplasts.

5. The method according to claim 1, wherein the aqueous medium comprising the population of plant cells comprises 2-80 nanomolar (nM) CAS-protein or CAS-like protein.

6. The method according to claim 1, wherein the CAS-protein or CAS-like protein is Cas9 or Cpf1.

7. The method according to claim 1, wherein the aqueous medium comprising the population of plant cells comprises 30-600 nanomolar (nM) CRISPR-Cas system guide RNA.

8. The method according to claim 1, wherein the molar ratio between the CAS-protein or CAS-like protein and CRISPR-Cas system guide RNA in the aqueous medium is from 1:300 to 8:3.

9. The method according to claim 1, wherein the aqueous medium comprising the population of plant cells comprises 100-400 mg/ml PEG.

10. The method according to claim 1, wherein the aqueous medium comprising the plant cells comprises:
    (a) 2-80 nanomolar (nM) CAS-protein or CAS-like protein,
    (b) 30-600 nanomolar (nM) CRISPR-Cas system guide RNA,
    (c) less than 0.01% (v/v) glycerol,
    (d) 100-400 mg/ml PEG, and
    (e) 10,000-2,000,000 plant cells/ml.

11. The method according to claim 1, wherein PEG is added to the aqueous medium after the CAS-protein or CAS-like protein and the CRISPR-Cas system guide RNA are provided to the medium.

12. The method according to claim 1, further comprising contacting the plants cells with a DNA oligonucleotide or DNA polynucleotide comprising the desired alteration to be introduced in the DNA molecule in the plant.

13. The method according to claim 1, wherein the population of plant cells is further cultivated in the presence of feeder plant cells.

14. The method according to claim 1, wherein individual protoplasts from the population of plant cells are further cultivated into plant calli, plant cells comprising a plant cell wall, and/or plants.

15. The method according to claim 1, wherein the targeted DNA molecule confers one or more of the following traits: herbicide tolerance, drought tolerance, male sterility, insect resistance, abiotic stress tolerance, modified fatty acid metabolism, modified carbohydrate metabolism, modified seed yield, modified oil percent, modified protein percent, and resistance to bacterial disease, fungal disease or viral disease.

16. The method according claim 1, wherein the aqueous medium does not comprise plasmid or vector material encoding for the CAS protein and/or CAS-like protein.

17. The method according to claim 4, wherein the population of plant protoplasts are tomato protoplasts.

18. The method according to claim 8, wherein the molar ratio between the CAS-protein or CAS-like protein and CRISPR-Cas system guide RNA in the aqueous medium is 1:20.

19. The method according to claim 1, wherein the aqueous medium comprising the population of plant cells is free of glycerol.

20. The method according to claim 13, wherein the feeder plant cells are plant protoplasts, wherein the feeder plant cells are of the same plant species as the population of plant cells, and wherein the feeder plant cells are provided in the form of a feeder disc containing 5,000-250,000 feeder plant cells.

* * * * *

SEQUENCE LISTING

<160> NUMBER OF SEQ ID NOS: 37

<210> SEQ ID NO 1
<211> LENGTH: 20
<212> TYPE: DNA
<213> ORGANISM: Lycopersicon esculentum

<400> SEQUENCE: 1
ttactgcatt ccatactcga                                          20

<210> SEQ ID NO 2
<211> LENGTH: 1435
<212> TYPE: PRT
<213> ORGANISM: Streptococcus pyogenes

<400> SEQUENCE: 2

Met Gly Trp Thr Leu Asn Ser Ala Gly Tyr Leu Leu Gly Lys Ile Asn
1               5                   10                  15

Leu Lys Ala Leu Ala Ala Leu Ala Lys Lys Ile Leu Ala Met Gly Ser
                20                  25                  30

Ser His His His His His Val Tyr Pro Tyr Asp Val Pro Asp Tyr
                35                  40                  45

Ala Glu Leu Pro Pro Lys Lys Lys Arg Lys Val Gly Ile Glu Asn Leu
    50                  55                  60

Tyr Phe Gln Gly Asp Lys Lys Tyr Ser Ile Gly Leu Asp Ile Gly Thr
65                  70                  75                  80

Asn Ser Val Gly Trp Ala Val Ile Thr Asp Glu Tyr Lys Val Pro Ser
                85                  90                  95

Lys Lys Phe Lys Val Leu Gly Asn Thr Asp Arg His Ser Ile Lys Lys
                100                 105                 110

Asn Leu Ile Gly Ala Leu Leu Phe Asp Ser Gly Glu Thr Ala Glu Ala
                115                 120                 125

Thr Arg Leu Lys Arg Thr Ala Arg Arg Arg Tyr Thr Arg Arg Lys Asn
    130                 135                 140

Arg Ile Cys Tyr Leu Gln Glu Ile Phe Ser Asn Glu Met Ala Lys Val
145                 150                 155                 160

Asp Asp Ser Phe Phe His Arg Leu Glu Glu Ser Phe Leu Val Glu Glu
                165                 170                 175

Asp Lys Lys His Glu Arg His Pro Ile Phe Gly Asn Ile Val Asp Glu
                180                 185                 190

Val Ala Tyr His Glu Lys Tyr Pro Thr Ile Tyr His Leu Arg Lys Lys
                195                 200                 205

Leu Val Asp Ser Thr Asp Lys Ala Asp Leu Arg Leu Ile Tyr Leu Ala
    210                 215                 220

Leu Ala His Met Ile Lys Phe Arg Gly His Phe Leu Ile Glu Gly Asp
225                 230                 235                 240

Leu Asn Pro Asp Asn Ser Asp Val Asp Lys Leu Phe Ile Gln Leu Val
                245                 250                 255

Gln Thr Tyr Asn Gln Leu Phe Glu Glu Asn Pro Ile Asn Ala Ser Gly
                260                 265                 270

Val Asp Ala Lys Ala Ile Leu Ser Ala Arg Leu Ser Lys Ser Arg Arg
                275                 280                 285

Leu Glu Asn Leu Ile Ala Gln Leu Pro Gly Glu Lys Lys Asn Gly Leu
    290                 295                 300

Phe Gly Asn Leu Ile Ala Leu Ser Leu Gly Leu Thr Pro Asn Phe Lys
305                 310                 315                 320

```
Ser Asn Phe Asp Leu Ala Glu Asp Ala Lys Leu Gln Leu Ser Lys Asp
            325                 330                 335

Thr Tyr Asp Asp Leu Asp Asn Leu Leu Ala Gln Ile Gly Asp Gln
            340                 345                 350

Tyr Ala Asp Leu Phe Leu Ala Ala Lys Asn Leu Ser Asp Ala Ile Leu
            355                 360                 365

Leu Ser Asp Ile Leu Arg Val Asn Thr Glu Ile Thr Lys Ala Pro Leu
370                 375                 380

Ser Ala Ser Met Ile Lys Arg Tyr Asp Glu His His Gln Asp Leu Thr
385                 390                 395                 400

Leu Leu Lys Ala Leu Val Arg Gln Gln Leu Pro Glu Lys Tyr Lys Glu
                405                 410                 415

Ile Phe Phe Asp Gln Ser Lys Asn Gly Tyr Ala Gly Tyr Ile Asp Gly
                420                 425                 430

Gly Ala Ser Gln Glu Glu Phe Tyr Lys Phe Ile Lys Pro Ile Leu Glu
                435                 440                 445

Lys Met Asp Gly Thr Glu Glu Leu Leu Val Lys Leu Asn Arg Glu Asp
                450                 455                 460

Leu Leu Arg Lys Gln Arg Thr Phe Asp Asn Gly Ser Ile Pro His Gln
465                 470                 475                 480

Ile His Leu Gly Glu Leu His Ala Ile Leu Arg Arg Gln Glu Asp Phe
                485                 490                 495

Tyr Pro Phe Leu Lys Asp Asn Arg Glu Lys Ile Glu Lys Ile Leu Thr
                500                 505                 510

Phe Arg Ile Pro Tyr Tyr Val Gly Pro Leu Ala Arg Gly Asn Ser Arg
                515                 520                 525

Phe Ala Trp Met Thr Arg Lys Ser Glu Glu Thr Ile Thr Pro Trp Asn
                530                 535                 540

Phe Glu Glu Val Val Asp Lys Gly Ala Ser Ala Gln Ser Phe Ile Glu
545                 550                 555                 560

Arg Met Thr Asn Phe Asp Lys Asn Leu Pro Asn Glu Lys Val Leu Pro
                565                 570                 575

Lys His Ser Leu Leu Tyr Glu Tyr Phe Thr Val Tyr Asn Glu Leu Thr
                580                 585                 590

Lys Val Lys Tyr Val Thr Glu Gly Met Arg Lys Pro Ala Phe Leu Ser
                595                 600                 605

Gly Glu Gln Lys Lys Ala Ile Val Asp Leu Leu Phe Lys Thr Asn Arg
                610                 615                 620

Lys Val Thr Val Lys Gln Leu Lys Glu Asp Tyr Phe Lys Lys Ile Glu
625                 630                 635                 640

Cys Phe Asp Ser Val Glu Ile Ser Gly Val Glu Asp Arg Phe Asn Ala
                645                 650                 655

Ser Leu Gly Thr Tyr His Asp Leu Leu Lys Ile Ile Lys Asp Lys Asp
                660                 665                 670

Phe Leu Asp Asn Glu Glu Asn Glu Asp Ile Leu Glu Asp Ile Val Leu
                675                 680                 685

Thr Leu Thr Leu Phe Glu Asp Arg Glu Met Ile Glu Glu Arg Leu Lys
                690                 695                 700

Thr Tyr Ala His Leu Phe Asp Asp Lys Val Met Lys Gln Leu Lys Arg
705                 710                 715                 720

Arg Arg Tyr Thr Gly Trp Gly Arg Leu Ser Arg Lys Leu Ile Asn Gly
                725                 730                 735
```

-continued

Ile Arg Asp Lys Gln Ser Gly Lys Thr Ile Leu Asp Phe Leu Lys Ser
            740                 745                 750

Asp Gly Phe Ala Asn Arg Asn Phe Met Gln Leu Ile His Asp Asp Ser
        755                 760                 765

Leu Thr Phe Lys Glu Asp Ile Gln Lys Ala Gln Val Ser Gly Gln Gly
    770                 775                 780

Asp Ser Leu His Glu His Ile Ala Asn Leu Ala Gly Ser Pro Ala Ile
785                 790                 795                 800

Lys Lys Gly Ile Leu Gln Thr Val Lys Val Val Asp Glu Leu Val Lys
                805                 810                 815

Val Met Gly Arg His Lys Pro Glu Asn Ile Val Ile Glu Met Ala Arg
            820                 825                 830

Glu Asn Gln Thr Thr Gln Lys Gly Gln Lys Asn Ser Arg Glu Arg Met
            835                 840                 845

Lys Arg Ile Glu Glu Gly Ile Lys Glu Leu Gly Ser Gln Ile Leu Lys
        850                 855                 860

Glu His Pro Val Glu Asn Thr Gln Leu Gln Asn Glu Lys Leu Tyr Leu
865                 870                 875                 880

Tyr Tyr Leu Gln Asn Gly Arg Asp Met Tyr Val Asp Gln Glu Leu Asp
                885                 890                 895

Ile Asn Arg Leu Ser Asp Tyr Asp Val Asp His Ile Val Pro Gln Ser
            900                 905                 910

Phe Leu Lys Asp Asp Ser Ile Asp Asn Lys Val Leu Thr Arg Ser Asp
        915                 920                 925

Lys Asn Arg Gly Lys Ser Asp Asn Val Pro Ser Glu Glu Val Val Lys
    930                 935                 940

Lys Met Lys Asn Tyr Trp Arg Gln Leu Leu Asn Ala Lys Leu Ile Thr
945                 950                 955                 960

Gln Arg Lys Phe Asp Asn Leu Thr Lys Ala Glu Arg Gly Gly Leu Ser
                965                 970                 975

Glu Leu Asp Lys Ala Gly Phe Ile Lys Arg Gln Leu Val Glu Thr Arg
            980                 985                 990

Gln Ile Thr Lys His Val Ala Gln Ile Leu Asp Ser Arg Met Asn Thr
        995                 1000                1005

Lys Tyr Asp Glu Asn Asp Lys Leu Ile Arg Glu Val Lys Val Ile
    1010                1015                1020

Thr Leu Lys Ser Lys Leu Val Ser Asp Phe Arg Lys Asp Phe Gln
    1025                1030                1035

Phe Tyr Lys Val Arg Glu Ile Asn Asn Tyr His His Ala His Asp
    1040                1045                1050

Ala Tyr Leu Asn Ala Val Val Gly Thr Ala Leu Ile Lys Lys Tyr
    1055                1060                1065

Pro Lys Leu Glu Ser Glu Phe Val Tyr Gly Asp Tyr Lys Val Tyr
    1070                1075                1080

Asp Val Arg Lys Met Ile Ala Lys Ser Glu Gln Glu Ile Gly Lys
    1085                1090                1095

Ala Thr Ala Lys Tyr Phe Phe Tyr Ser Asn Ile Met Asn Phe Phe
    1100                1105                1110

Lys Thr Glu Ile Thr Leu Ala Asn Gly Glu Ile Arg Lys Arg Pro
    1115                1120                1125

Leu Ile Glu Thr Asn Gly Glu Thr Gly Glu Ile Val Trp Asp Lys
    1130                1135                1140

Gly Arg Asp Phe Ala Thr Val Arg Lys Val Leu Ser Met Pro Gln

```
                1145                1150                1155
Val Asn Ile Val Lys Lys Thr Glu Val Gln Thr Gly Gly Phe Ser
        1160                1165                1170
Lys Glu Ser Ile Leu Pro Lys Arg Asn Ser Asp Lys Leu Ile Ala
        1175                1180                1185
Arg Lys Lys Asp Trp Asp Pro Lys Lys Tyr Gly Gly Phe Asp Ser
        1190                1195                1200
Pro Thr Val Ala Tyr Ser Val Leu Val Val Ala Lys Val Glu Lys
        1205                1210                1215
Gly Lys Ser Lys Lys Leu Lys Ser Val Lys Glu Leu Leu Gly Ile
        1220                1225                1230
Thr Ile Met Glu Arg Ser Ser Phe Glu Lys Asn Pro Ile Asp Phe
        1235                1240                1245
Leu Glu Ala Lys Gly Tyr Lys Glu Val Lys Lys Asp Leu Ile Ile
        1250                1255                1260
Lys Leu Pro Lys Tyr Ser Leu Phe Glu Leu Glu Asn Gly Arg Lys
        1265                1270                1275
Arg Met Leu Ala Ser Ala Gly Glu Leu Gln Lys Gly Asn Glu Leu
        1280                1285                1290
Ala Leu Pro Ser Lys Tyr Val Asn Phe Leu Tyr Leu Ala Ser His
        1295                1300                1305
Tyr Glu Lys Leu Lys Gly Ser Pro Glu Asp Asn Glu Gln Lys Gln
        1310                1315                1320
Leu Phe Val Glu Gln His Lys His Tyr Leu Asp Glu Ile Ile Glu
        1325                1330                1335
Gln Ile Ser Glu Phe Ser Lys Arg Val Ile Leu Ala Asp Ala Asn
        1340                1345                1350
Leu Asp Lys Val Leu Ser Ala Tyr Asn Lys His Arg Asp Lys Pro
        1355                1360                1365
Ile Arg Glu Gln Ala Glu Asn Ile Ile His Leu Phe Thr Leu Thr
        1370                1375                1380
Asn Leu Gly Ala Pro Ala Ala Phe Lys Tyr Phe Asp Thr Thr Ile
        1385                1390                1395
Asp Arg Lys Arg Tyr Thr Ser Thr Lys Glu Val Leu Asp Ala Thr
        1400                1405                1410
Leu Ile His Gln Ser Ile Thr Gly Leu Tyr Glu Thr Arg Ile Asp
        1415                1420                1425
Leu Ser Gln Leu Gly Gly Asp
        1430                1435

<210> SEQ ID NO 3
<211> LENGTH: 4173
<212> TYPE: DNA
<213> ORGANISM: Streptococcus pyogenes

<400> SEQUENCE: 3
atgggaagag gatcgcatca ccaccatcat cataagcttc aaagaagaa gaggaaggtt      60 ctcgagatgg ataagaagta ctctatcgga cttgatatcg gaactaactc tgtgggatgg     120
gctgtgatca ctgatgagta caaggtgcca tctaagaagt tcaaggtttt gggaaacact     180
gataggcact ctatcaagaa aaaccttatc ggagctttgc ttttcgattc tggtgagact     240
gctgaggcta ctaggcttaa gaggactgct agaagaaggt acactagaag aaagaacagg     300
atctgctacc ttcaagagat cttctctaac gagatggcta aagtggatga ttcattcttc     360
```

-continued

```
cacaggcttg aagagtcttt cttggtggaa gaagataaga agcacgagag gcacccaatc    420
ttcggaaaca tcgttgatga ggtggcatac cacgagaagt acccaactat ctaccacctt    480
aggaagaagc ttgttgattc tactgataag gctgatctta ggcttatcta ccttgctctt    540
gctcacatga tcaagttcag gggacacttc cttatcgagg gtgatcttaa cccagataac    600
tctgatgtgg ataagctttt catccagctt gtgcagactt acaaccagct tttcgaagag    660
aacccaatca acgcttctgg tgtggatgct aaggctatcc tttctgctag gctttctaag    720
tctagaaggc ttgagaacct tattgctcag cttccaggtg agaagaagaa cggactttc    780 ggaaacttga tcgctctttc tcttggactt actccaaact tcaagtctaa cttcgatctt    840
gctgaggatg caaagcttca gttgtctaag gatacttacg atgatgatct tgataacttg    900
cttgctcaga tcggagatca gtacgctgat cttttccttg ctgctaaaaa ctttctgat    960 gctatcttgc tttctgatat ccttagggtg aacactgaga tcactaaggc tccactttct   1020
gcttctatga tcaagaggta cgatgagcac caccaggatc ttactttgct taaggctctt   1080
gtgaggcagc agttgccaga gaagtacaaa gagattttct tcgatcagtc taagaacgga   1140
tacgctggtt acatcgatgg tggtgcatct caagaagagt tctacaagtt catcaagcca   1200
atccttgaga gatggatgg aactgaagag ttgcttgtga gcttaacag agaggatctt   1260 cttaggaagc agaggacttt cgataacgga tctatccctc accagatcca ccttggagag   1320
cttcacgcta tcttgagaag gcaagaggat ttctacccat tcttgaagga taacaggaa   1380 aaaatcgaga agattcttac tttcaggatc ccttactacg tgggaccact tgctagggga   1440
aattctaggt tcgcttggat gactaggaag tctgaagaga ctatcactcc atggaacttc   1500
gaagaggtgg tggataaggg tgctagtgct cagtctttca tcgagaggat gacaaacttc   1560
gataagaacc ttccaaacga gaaggtgttg ccaaagcact ctttgcttta cgagtacttc   1620
actgtgtaca acgagcttac taaggtgaag tacgtgacag agggaatgag gaagccagct   1680
ttcttgtctg gtgagcaaaa gaaggctatc gttgatcttt tgttcaagac taatagaaag   1740
gtgacagtga agcagcttaa agaggattac ttcaaaaaga tcgagtgctt cgattcagtt   1800
gagatctctg tgttgagga taggttcaac gcatcttgg gaacttacca cgatttgttg   1860
aagattatca aggataagga tttcttggat aacgaggaaa acgaggatat cttggaggat   1920
atcgtgctta ctcttactct tttcgaggat agagagatga ttgaagaaag gcttaaaact   1980
tacgctcacc ttttcgatga taaggtgatg aagcagttga agagaagaag atacacaggt   2040
tggggaaggt tgtctaggaa gcttatcaac ggaatcaggg ataagcagtc tggtaagact   2100
atcttggatt tccttaagtc tgatggattc gctaatagga acttcatgca gttgatccac   2160
gatgattctt tgactttcaa agaggatatc cagaaggctc aggtttcagg acagggtgat   2220
agtttacacg agcacattgc taaccttgct ggatctcctg caatcaagaa gggaatcttg   2280
cagactgtga aggttgtgga tgagttggtg aaggtgatgg gaaggcataa gccagagaac   2340
atcgtgatcg aaatggctag agagaaccag actactcaga agggacagaa gaactctagg   2400
gaaaggatga gaggatcga gagggaatc aaagagcttg gatctcagat ccttaaagag   2460
cacccagttg agaacactca gcttcagaac gagaagcttt acctttacta cttgcagaac   2520
ggaagggata tgtatgtgga tcaagagttg gatatcaaca ggttgtctga ttatgatgtt   2580
gatcacatcg tgccacagtc ttttttgaag gatgattcta tcgataacaa ggtgttgact   2640
aggtctgata gaacaggggg aaagtctgat aacgttccat ctgaagaggt tgtgaaaaag   2700
atgaagaact attggaggca gcttcttaac gctaagttga tcactcagag gaagttcgat   2760
```

```
aatttgacta aggctgagag gggaggattg tctgagcttg ataaggcagg attcatcaag    2820
aggcagttgg ttgagactag gcagatcaca agcacgtgg cacagatcct tgattctagg    2880
atgaacacta agtatgatga aacgataag ttaatcaggg aagttaaggt gatcactttg    2940
aagtctaagc ttgtgtctga ttttaggaag gatttccaat tctacaaggt gagagagatc    3000
aacaactacc accacgctca cgatgcttac cttaacgctg ttgtgggaac tgctttgatc    3060
aagaagtatc caaagttgga gtctgagttc gtgtacggtg attacaaggt gtacgatgtg    3120
aggaagatga tcgctaagtc agagcaagag atcggaaagg ctactgctaa gtatttcttc    3180
tactctaaca tcatgaattt cttcaagaca gagatcactc ttgctaacgg tgagattagg    3240
aagaggccac ttatcgagac aaatggtgag acaggtgaga tcgtgtggga taggggaagg    3300
gatttcgcta ctgtgagaaa ggtgttgtct atgccacagg tgaacattgt gaagaaaact    3360
gaggtgcaga ctggtggatt ctctaaagag tctatccttc caaagaggaa ctctgataag    3420
ttgattgcta ggaaaaagga ttgggatcca aaaaagtacg gtggattcga ttctccaact    3480
gtggcttact ctgtgcttgt ggtggctaag gttgagaagg gaaaatcaaa gaaattgaag    3540
tctgtgaaag agcttcttgg aatcactatc atggaaaggt catctttcga gaagaaccct    3600
atcgatttcc ttgaggctaa gggatacaaa gaggtgaaga aggatcttat catcaagctt    3660
ccaaagtact cacttttcga gcttgagaat ggaagaaaga ggatgcttgc ttctgctggt    3720
gagttgcaga agggtaacga acttgctttg ccttctaagt acgttaactt cctttacctt    3780
gcttctcact acgagaagtt gaagggatct ccagaggata cgaacaaaa gcagttgttc    3840 gttgagcagc acaagcacta ccttgatgag atcatcgagc agatctctga gttctctaag    3900
agggttatct tggctgatgc aaaccttgat aaggtgttga gtgcttacaa caaacatagg    3960
gataagccaa tcagagagca ggctgagaac atcatccacc ttttcacttt gactaacctt    4020
ggtgctccag ctgcttttcaa gtacttcgat acaactattg atagaaagag gtacacttct    4080
acaaaagagg ttttggatgc tacttttgatc caccagagta tcactggact ttacgagact    4140
aggatcgatt tgtctcagct tggtggtgat tga                                4173
```

<210> SEQ ID NO 4  
<211> LENGTH: 221  
<212> TYPE: DNA  
<213> ORGANISM: Artificial Sequence  
<220> FEATURE:  
<223> OTHER INFORMATION: Encodes sgRNA of tomato Lycopersicon esculentum locus 3g095310 fused to Arabidopsis thalian U6 PolIII promoter sequence

<400> SEQUENCE: 4

```
ggagtgatca aaagtcccac atcgatcagg tgatatatag cagcttagtt tatataatga     60
tagagtcgac atagcgattg ttactgcatt ccatactcga gttttagagc tagaaatagc    120
aagttaaaat aaggctagtc cgttatcaac ttgaaaaagt ggcaccgagt cggtgctttt    180
tttctagacc cagctttctt gtacaaagtt ggcattacgc t                       221
```

<210> SEQ ID NO 5  
<211> LENGTH: 44  
<212> TYPE: DNA  
<213> ORGANISM: Artificial Sequence  
<220> FEATURE:  
<223> OTHER INFORMATION: Forward primer sequence T7-3g095310

<400> SEQUENCE: 5

-continued

```
ggatcctaat acgactcact atagttactg cattccatac tcga          44
```

<210> SEQ ID NO 6
<211> LENGTH: 19
<212> TYPE: DNA
<213> ORGANISM: Artificial Sequence
<220> FEATURE:
<223> OTHER INFORMATION: Reverse primer sequence sgRev

<400> SEQUENCE: 6

```
aaaaaaagca ccgactcgg                                      19
```

<210> SEQ ID NO 7
<211> LENGTH: 21
<212> TYPE: DNA
<213> ORGANISM: Artificial Sequence
<220> FEATURE:
<223> OTHER INFORMATION: Forward primer for 03g095310

<400> SEQUENCE: 7

```
aaggtgaagg gggtaaaatg g                                   21
```

<210> SEQ ID NO 8
<211> LENGTH: 22
<212> TYPE: DNA
<213> ORGANISM: Artificial Sequence
<220> FEATURE:
<223> OTHER INFORMATION: Reverse primer for 03g095310

<400> SEQUENCE: 8

```
gaaggtgaag ggggtaaaat gg                                  22
```

<210> SEQ ID NO 9
<211> LENGTH: 20
<212> TYPE: DNA
<213> ORGANISM: Lycopersicon esculentum

<400> SEQUENCE: 9

```
ttactgcatt ccatactcga                                     20
```

<210> SEQ ID NO 10
<211> LENGTH: 18
<212> TYPE: DNA
<213> ORGANISM: Artificial Sequence
<220> FEATURE:
<223> OTHER INFORMATION: Modified sequence relative to SEQ ID NO:9

<400> SEQUENCE: 10

```
ttactgcatt ccatacga                                       18
```

<210> SEQ ID NO 11
<211> LENGTH: 12
<212> TYPE: DNA
<213> ORGANISM: Artificial Sequence
<220> FEATURE:
<223> OTHER INFORMATION: Modified sequence relative to SEQ ID NO:9

<400> SEQUENCE: 11

```
ttactgcatc ga                                             12
```

<210> SEQ ID NO 12
<211> LENGTH: 13
<212> TYPE: DNA
<213> ORGANISM: Artificial Sequence
<220> FEATURE:
<223> OTHER INFORMATION: Modified sequence relative to SEQ ID NO:9

```
<400> SEQUENCE: 12
ttactgcatt cca                                                      13

<210> SEQ ID NO 13
<211> LENGTH: 19
<212> TYPE: DNA
<213> ORGANISM: Artificial Sequence
<220> FEATURE:
<223> OTHER INFORMATION: Modified sequence relative to SEQ ID NO:9

<400> SEQUENCE: 13
ttactgcatt ccataccga                                                19

<210> SEQ ID NO 14
<211> LENGTH: 17
<212> TYPE: DNA
<213> ORGANISM: Artificial Sequence
<220> FEATURE:
<223> OTHER INFORMATION: Modified sequence relative to SEQ ID NO:9

<400> SEQUENCE: 14
ttactgcatt ccatcga                                                  17

<210> SEQ ID NO 15
<211> LENGTH: 14
<212> TYPE: DNA
<213> ORGANISM: Artificial Sequence
<220> FEATURE:
<223> OTHER INFORMATION: Modified sequence relative to SEQ ID NO:9

<400> SEQUENCE: 15
ttactgcatt tcga                                                     14

<210> SEQ ID NO 16
<211> LENGTH: 12
<212> TYPE: DNA
<213> ORGANISM: Artificial Sequence
<220> FEATURE:
<223> OTHER INFORMATION: Modified sequence relative to SEQ ID NO:9

<400> SEQUENCE: 16
ttactgcatc ga                                                       12

<210> SEQ ID NO 17
<211> LENGTH: 15
<212> TYPE: DNA
<213> ORGANISM: Artificial Sequence
<220> FEATURE:
<223> OTHER INFORMATION: Modified sequence relative to SEQ ID NO:9

<400> SEQUENCE: 17
ttactgcatt cccga                                                    15

<210> SEQ ID NO 18
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 18
ttactgcatt ccatacttcg                                               20

<210> SEQ ID NO 19
```

```
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 19
ttactgcatt ccatacttcg                                              20

<210> SEQ ID NO 20
<211> LENGTH: 17
<212> TYPE: DNA
<213> ORGANISM: Artificial Sequence
<220> FEATURE:
<223> OTHER INFORMATION: Modified sequence relative to SEQ ID NO:9

<400> SEQUENCE: 20
ttactgcatt ccatcga                                                 17

<210> SEQ ID NO 21
<211> LENGTH: 13
<212> TYPE: DNA
<213> ORGANISM: Artificial Sequence
<220> FEATURE:
<223> OTHER INFORMATION: Modified sequence relative to SEQ ID NO:9

<400> SEQUENCE: 21
ttactgcatt cga                                                     13

<210> SEQ ID NO 22
<211> LENGTH: 19
<212> TYPE: DNA
<213> ORGANISM: Artificial Sequence
<220> FEATURE:
<223> OTHER INFORMATION: Modified sequence relative to SEQ ID NO:9

<400> SEQUENCE: 22
ttactgcatt ccataccga                                               19

<210> SEQ ID NO 23
<211> LENGTH: 19
<212> TYPE: DNA
<213> ORGANISM: Artificial Sequence
<220> FEATURE:
<223> OTHER INFORMATION: Modified sequence relative to SEQ ID NO:9

<400> SEQUENCE: 23
ttactgcatt ccataccga                                               19

<210> SEQ ID NO 24
<211> LENGTH: 13
<212> TYPE: DNA
<213> ORGANISM: Artificial Sequence
<220> FEATURE:
<223> OTHER INFORMATION: Modified sequence relative to SEQ ID NO:9

<400> SEQUENCE: 24
ttactgcatt cga                                                     13

<210> SEQ ID NO 25
<211> LENGTH: 19
<212> TYPE: DNA
<213> ORGANISM: Artificial Sequence
<220> FEATURE:
<223> OTHER INFORMATION: Modified sequence relative to SEQ ID NO:9

<400> SEQUENCE: 25
```

```
ttactgcatt ccatatcga                                             19

<210> SEQ ID NO 26
<211> LENGTH: 13
<212> TYPE: DNA
<213> ORGANISM: Artificial Sequence
<220> FEATURE:
<223> OTHER INFORMATION: Modified sequence relative to SEQ ID NO:9

<400> SEQUENCE: 26
ttactgcatt cga                                                   13

<210> SEQ ID NO 27
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 27
ttactgcatt ccatacttcg                                            20

<210> SEQ ID NO 28
<211> LENGTH: 15
<212> TYPE: DNA
<213> ORGANISM: Artificial Sequence
<220> FEATURE:
<223> OTHER INFORMATION: Modified sequence relative to SEQ ID NO:9

<400> SEQUENCE: 28
ttactgcatt cccga                                                 15

<210> SEQ ID NO 29
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 29
ttactgcatt ccatacttcg                                            20

<210> SEQ ID NO 30
<211> LENGTH: 15
<212> TYPE: DNA
<213> ORGANISM: Artificial Sequence
<220> FEATURE:
<223> OTHER INFORMATION: Modified sequence relative to SEQ ID NO:9

<400> SEQUENCE: 30
ttactgcatt cccga                                                 15

<210> SEQ ID NO 31
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 31
ttactgcatt ccatacttcg                                            20

<210> SEQ ID NO 32
<211> LENGTH: 10
<212> TYPE: DNA
```

```
<213> ORGANISM: Artificial Sequence
<220> FEATURE:
<223> OTHER INFORMATION: Modified sequence relative to SEQ ID NO:9

<400> SEQUENCE: 32
ttactgtcga                                                              10

<210> SEQ ID NO 33
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 33
ttactgcatt ccatacttcg                                                   20

<210> SEQ ID NO 34
<211> LENGTH: 12
<212> TYPE: DNA
<213> ORGANISM: Artificial Sequence
<220> FEATURE:
<223> OTHER INFORMATION: Modified sequence relative to SEQ ID NO:9

<400> SEQUENCE: 34
ttactgcatc ga                                                           12

<210> SEQ ID NO 35
<211> LENGTH: 19
<212> TYPE: DNA
<213> ORGANISM: Artificial Sequence
<220> FEATURE:
<223> OTHER INFORMATION: Modified sequence relative to SEQ ID NO:9

<400> SEQUENCE: 35
ttactgcatt ccataccga                                                    19

<210> SEQ ID NO 36
<211> LENGTH: 20
<212> TYPE: DNA
<213> ORGANISM: Artificial Sequence
<220> FEATURE:
<223> OTHER INFORMATION: Modified sequence relative to SEQ ID NO:9

<400> SEQUENCE: 36
ttactgcatt ccatacttcg                                                   20

<210> SEQ ID NO 37
<211> LENGTH: 14
<212> TYPE: DNA
<213> ORGANISM: Artificial Sequence
<220> FEATURE:
<223> OTHER INFORMATION: Modified sequence relative to SEQ ID NO:9

<400> SEQUENCE: 37
ttactgcatt tcga                                                         14
```